(12) United States Patent
Berner et al.

(10) Patent No.: US 8,475,813 B2
(45) Date of Patent: Jul. 2, 2013

(54) METHODS OF TREATMENT USING A GASTRIC RETAINED GABAPENTIN DOSAGE

(75) Inventors: Bret Berner, Half Moon Bay, CA (US); Sui Yuen Eddie Hou, Foster City, CA (US)

(73) Assignee: Depomed, Inc., Newark, CA (US)

( * ) Notice: Subject to any disclaimer, the term of this patent is extended or adjusted under 35 U.S.C. 154(b) by 0 days.

(21) Appl. No.: 13/301,570

(22) Filed: Nov. 21, 2011

(65) Prior Publication Data

US 2012/0128735 A1    May 24, 2012

Related U.S. Application Data

(60) Continuation of application No. 13/270,126, filed on Oct. 10, 2011, which is a division of application No. 12/563,781, filed on Sep. 21, 2009, now Pat. No. 8,119,166, which is a division of application No. 10/903,879, filed on Jul. 30, 2004, now Pat. No. 7,612,112, which is a continuation-in-part of application No. 10/280,309, filed on Oct. 25, 2002, now Pat. No. 7,438,927.

(60) Provisional application No. 60/335,248, filed on Oct. 25, 2001.

(51) Int. Cl.
| | |
|---|---|
| A61K 31/195 | (2006.01) |
| A61K 33/00 | (2006.01) |
| A61K 31/55 | (2006.01) |
| A61K 31/5415 | (2006.01) |
| A61K 31/519 | (2006.01) |
| A61K 31/197 | (2006.01) |
| A61K 31/5513 | (2006.01) |

(52) U.S. Cl.
USPC ........... 424/400; 424/497; 424/722; 514/561; 514/567; 514/564; 514/217; 514/225.8; 514/221; 514/259.41

(58) Field of Classification Search
USPC .................. 424/400, 497, 722; 514/561, 564, 514/567, 217, 225.8, 221, 259.41
See application file for complete search history.

(56) References Cited

U.S. PATENT DOCUMENTS

| | | |
|---|---|---|
| 3,574,820 A | 4/1971 | Johnson et al. |
| 3,845,770 A | 11/1974 | Theeuwes et al. |
| 3,977,404 A | 8/1976 | Theeuwes |
| 4,024,175 A | 5/1977 | Satzinger et al. |
| 4,087,544 A | 5/1978 | Satzinger et al. |
| 4,152,326 A | 5/1979 | Hartenstein et al. |
| 4,309,406 A | 1/1982 | Guley et al. |

(Continued)

FOREIGN PATENT DOCUMENTS

| | | |
|---|---|---|
| CA | 2220038 | 7/1999 |
| CA | 2143500 | 4/2007 |

(Continued)

OTHER PUBLICATIONS

U.S. Appl. No. 09/425,491, Shell et al.

(Continued)

*Primary Examiner* — Aradhana Sasan
(74) *Attorney, Agent, or Firm* — McDermott Will & Emery LLP

(57) ABSTRACT

A method of treatment for epilepsy and other disease states is described, which comprises delivery of gabapentin in a gastric retained dosage form.

18 Claims, 2 Drawing Sheets

U.S. PATENT DOCUMENTS

| | | | |
|---|---|---|---|
| 4,404,183 A | 9/1983 | Kawata et al. |
| 4,462,839 A | 7/1984 | McGinley et al. |
| 4,612,008 A | 9/1986 | Wong et al. |
| 4,753,801 A | 6/1988 | Oren et al. |
| 4,828,836 A | 5/1989 | Elger et al. |
| 4,851,232 A | 7/1989 | Urquhart et al. |
| 4,871,548 A | 10/1989 | Edgren et al. |
| 4,894,476 A | 1/1990 | Butler et al. |
| 4,996,058 A | 2/1991 | Sinnreich et al. |
| 5,007,790 A | 4/1991 | Shell |
| 5,084,479 A | 1/1992 | Woodruff et al. |
| 5,232,704 A | 8/1993 | Franz et al. |
| 5,273,758 A | 12/1993 | Royce |
| 5,382,435 A | 1/1995 | Geary et al. |
| 5,443,843 A | 8/1995 | Curatolo et al. |
| 5,558,879 A | 9/1996 | Chen et al. |
| 5,582,837 A | 12/1996 | Shell |
| 5,591,452 A | 1/1997 | Miller et al. |
| 5,660,861 A | 8/1997 | Jao et al. |
| 5,783,212 A | 7/1998 | Fassihi et al. |
| 5,872,984 A | 2/1999 | Berglund et al. |
| 5,906,832 A | 5/1999 | Jao et al. |
| 5,945,125 A | 8/1999 | Kim |
| 5,955,103 A | 9/1999 | Jao et al. |
| 5,972,389 A | 10/1999 | Shell et al. |
| 6,024,977 A | 2/2000 | Yatvin et al. |
| 6,024,982 A | 2/2000 | Oshlack et al. |
| 6,054,482 A | 4/2000 | Augart et al. |
| 6,068,859 A | 5/2000 | Curatolo et al. |
| 6,117,453 A | 9/2000 | Seth et al. |
| 6,120,803 A | 9/2000 | Wong et al. |
| 6,162,466 A | 12/2000 | Licht et al. |
| 6,187,338 B1 | 2/2001 | Caruso et al. |
| 6,242,488 B1 | 6/2001 | Bueno et al. |
| 6,255,526 B1 | 7/2001 | Pesachovich et al. |
| 6,273,340 B1 | 8/2001 | Rivailler et al. |
| 6,294,192 B1 | 9/2001 | Patel et al. |
| 6,294,198 B1 | 9/2001 | Vilkov |
| 6,294,690 B1 | 9/2001 | Deering et al. |
| 6,310,098 B1 | 10/2001 | Guttuso, Jr. |
| 6,333,352 B1 | 12/2001 | Derakshan |
| 6,340,475 B2 | 1/2002 | Shell et al. |
| 6,346,270 B1 | 2/2002 | Shivanand et al. |
| 6,350,471 B1 | 2/2002 | Seth |
| 6,451,808 B1 | 9/2002 | Cowles |
| 6,465,012 B2 | 10/2002 | Vilkov |
| 6,488,962 B1 | 12/2002 | Berner et al. |
| 6,488,964 B2 | 12/2002 | Bruna et al. |
| 6,635,280 B2 | 10/2003 | Shell et al. |
| 6,635,281 B2 | 10/2003 | Wong et al. |
| 6,682,759 B2 | 1/2004 | Lim et al. |
| 6,683,112 B2 | 1/2004 | Chen et al. |
| 6,723,340 B2 | 4/2004 | Gusler et al. |
| 7,438,927 B2 | 10/2008 | Berner et al. |
| 7,612,112 B2 | 11/2009 | Berner et al. |
| 7,731,989 B2 | 6/2010 | Berner et al. |
| 8,119,166 B2 | 2/2012 | Berner et al. |
| 8,192,756 B2 | 6/2012 | Berner et al. |
| 2001/0004644 A1 | 6/2001 | Levine |
| 2001/0008889 A1 | 7/2001 | Caruso et al. |
| 2001/0036943 A1 | 11/2001 | Coe et al. |
| 2001/0043946 A1 | 11/2001 | Vilkov |
| 2001/0046473 A1 | 11/2001 | Besse |
| 2001/0055607 A1 | 12/2001 | Levine |
| 2002/0012679 A1 | 1/2002 | Bruna et al. |
| 2002/0012680 A1 | 1/2002 | Patel et al. |
| 2002/0082252 A1 | 6/2002 | Hochman |
| 2002/0107208 A1 | 8/2002 | Chen et al. |
| 2002/0115705 A1 | 8/2002 | Magnus-Miller et al. |
| 2002/0142050 A1 | 10/2002 | Straub et al. |
| 2003/0031711 A1 | 2/2003 | Fara et al. |
| 2003/0044466 A1 | 3/2003 | Markey et al. |
| 2003/0064036 A1 | 4/2003 | Petereit et al. |
| 2003/0091630 A1 | 5/2003 | Louie-Helm et al. |
| 2003/0100611 A1 | 5/2003 | Berner et al. |
| 2003/0104052 A1 | 6/2003 | Berner et al. |
| 2003/0104053 A1 | 6/2003 | Gusler et al. |
| 2003/0104062 A1 | 6/2003 | Berner et al. |
| 2003/0133985 A1 | 7/2003 | Louie-Helm et al. |
| 2003/0152622 A1 | 8/2003 | Louie-Helm et al. |
| 2003/0181390 A1 | 9/2003 | Gallop et al. |
| 2004/0062802 A1 | 4/2004 | Hermelin |
| 2004/0180088 A1 | 9/2004 | Dudhara et al. |
| 2004/0185105 A1 | 9/2004 | Berner et al. |
| 2005/0064036 A1 | 3/2005 | Berner et al. |
| 2005/0158380 A1 | 7/2005 | Chawla et al. |
| 2006/0094785 A1 | 5/2006 | Guttoso, Jr. |
| 2006/0159743 A1 | 7/2006 | Berner et al. |
| 2006/0264509 A1 | 11/2006 | Fraser et al. |
| 2007/0184104 A1 | 8/2007 | Berner et al. |
| 2009/0017121 A1 | 1/2009 | Berner et al. |
| 2009/0176882 A1 | 7/2009 | Berner et al. |
| 2010/0247610 A1 | 9/2010 | Berner et al. |
| 2011/0218246 A1 | 9/2011 | Berner et al. |
| 2012/0027823 A1 | 2/2012 | Berner et al. |
| 2012/0064129 A1 | 3/2012 | Berner et al. |
| 2012/0064168 A1 | 3/2012 | Berner et al. |
| 2012/0128735 A1 | 5/2012 | Berner et al. |

FOREIGN PATENT DOCUMENTS

| | | | |
|---|---|---|---|
| DE | 4432757 A1 | 3/1996 |
| EP | 0458751 A1 | 5/1991 |
| EP | 1118321 | 7/2001 |
| WO | WO 90/11757 A1 | 10/1990 |
| WO | WO 92/04013 A1 | 3/1992 |
| WO | WO 93/18755 A1 | 3/1992 |
| WO | WO 95/29665 A1 | 11/1995 |
| WO | WO 96/26718 A2 | 9/1996 |
| WO | WO 96/32097 A1 | 10/1996 |
| WO | WO 97/18814 A1 | 5/1997 |
| WO | WO 97/47285 A1 | 12/1997 |
| WO | WO 98/11879 A1 | 3/1998 |
| WO | WO 98/55107 A1 | 12/1998 |
| WO | WO 98/56360 A1 | 12/1998 |
| WO | WO 99/12537 A1 | 9/1999 |
| WO | WO 99/47128 A1 | 9/1999 |
| WO | WO 00/53225 A1 | 9/2000 |
| WO | WO 00/59477 A1 | 10/2000 |
| WO | WO 00/76478 A1 | 12/2000 |
| WO | WO 01/13894 A1 | 3/2001 |
| WO | WO 01/37812 A1 | 5/2001 |
| WO | WO 01/56544 A2 | 8/2001 |
| WO | WO 01/97612 A1 | 12/2001 |
| WO | WO 01/97782 A1 | 12/2001 |
| WO | WO 03/002101 A1 | 1/2003 |
| WO | WO 03/002151 A1 | 1/2003 |
| WO | WO 03/011255 A1 | 2/2003 |
| WO | WO 03/035040 | 5/2003 |

OTHER PUBLICATIONS

U.S. Appl. No. 10/045,816, filed Oct. 25, 2001, Berner et al.

Adler, "Treatment of restless legs syndrome with gabapentin", Clin. Neuropharmacol., vol. 20, No. 2, pp. 148-151 (1997).

Andrews et al., "Gabapentin: a new agent for the management of epilepsy", Ann. Pharmacother., vol. 28, pp. 1188-1196 (1994).

Asconape et al., "Myclonus associated with the use of gabapentin", Epilepsia, vol. 41, pp. 479-481(2000).

Ashton et al., "GABA-ergic drugs: exit stage left, enter stage right", Journal of Psychopharmacology, vol. 17, No. 2, pp. 174-178 (2003).

Backonja et al., "Gabapentin for the symptomatic treatment of painful neuropathy in patients with diabetes milletus", JAMA, vol. 280, pp. 1831-1836 (1998).

Bebin et al., "New anticonvulsant drug: focus on flunarizine, fosphenytoin, midazolam and stiripentol", Drugs, vol. 48, pp. 153-171 (1994).

Benedetti, "Enzyme induction and inhibition by new antiepileptic drugs: a review of human studies", Fund. Clin. Pharmac., vol. 14, pp. 301-319 (2000).

Benetello et al., "Oral gabapentin disposition in patients with epilepsy after a high-protein meal", Epilepsia, vol. 38, No. 10, pp. 1140-1142 (1997).

Ben-Menachem, "New antiepileptic drugs and non-pharmacological treatments"; Curr. Opin. Neurol., vol. 13, pp. 165-170 (2000).

Bennett et al., "Gabapentin in the treatment of neurophathic pain", Palliative Med., vol. 18, No. 1, pp. 5-11 (2004).

Bennett et al., "Future directions in the management of pain by intraspinal drug deiivery", J. Pain and Symptom Management, vol. 20, No. 2, pp. S44-S50 (2000).

Bernus et al., "Anticonvulsent therapy in aged patients, clinical pharmacokinetic considerations", Drugs & Aging, vol. 10, pp. 278-289 (1997).

Beydoun, "Monotherapy trial of new antiepileptic drugs", Epilepsia, vol. 38, No. 9, pp. S21-S31 (1997).

Bialer, "Comparative pharmacokinetics of the newer antiepileptic drugs", Clin. Pharmacokinet., vol. 24, pp. 441-452 (1993).

Blum et al., "Pharmacokinetics of gabapentin in subject with various degrees of renal function", Clin, Pharmacol. Ther., vol. 56, pp. 154-159 (1994).

Bourgeois, "Important pharmacokinetic properties of antiepileptic drugs", Epilepsia, vol. 36, pp. 5, pp. S1-S7 (1995).

Bourgeois, "New antiepileptic drugs", Arch. Neurol. vol. 55. pp. 1181-1183 (1998).

Bourgeois, "Pharmacokinetic properties of current antiepileptic drugs: what improvements are needed?", Neurology, vol. 55, No. 3, pp. S11-S16 (2000).

Boyd et al., "Clinical research: effects of age and gender on single-dose pharmacokinetics of gabapentin," Epilepsia, vol. 40, pp. 474-479 (1999).

Brown et al., "Cloning and deletion mutagenesis of the $\alpha_2\delta$ calcium channel subunit from porcine cerebral cortex", J. Biol. Chem., vol. 273, pp. 25458-25465 (1998).

Browne, "Long-term efficacy and toxicity of gabapentin", Neurology, vol. 43, pp. A307 (1993).

Bryans et al., "3-substitute GABA analogs with central nervous system activity: A review", Medicinal Research Reviews, vol. 19, No. 2, pp. 149-177 (1999).

Chadwick et al., "Clinical administration of new antiepileptic drugs, an overview of safety and efficacy", Epilepsia, vol. 37, No. 6, pp. S17-S22 (1996).

Chadwick, "An overview of the efficacy and tolerability of new antiepileptic drugs", Epilepsia, vol. 38, No. 1, pp. S59-S62 (1997).

Chadwick, "Gabapentin", Lancet, vol. 343, pp. 89-91 (1994).

Cramer et al., "New antiepileptic drugs: comparison of key clinical trials", Epilepsia, vol. 40, pp. 590-600 (1999).

Curry et al. "Newer antiepileptic drugs: gabapentin, felbamate, topirimate and fosphenytoin", Am. Family Physician, vol. 57, pp. 513-520 (1998).

Davis et al., "Relationship between the rate of appearance of oxyprenolol in the systematic circulation and the location of an oxyprenolol oros 16/260 drug delivery system within the gastrointestinal tract as determined by scintigraphy",Br. J. Clin. Pharmac., vol. 26, pp. 435-443 (1988).

Davis et al., "Transit of pharmaceutical dosage forms through the small intestine", Gut. vol. 27, pp. 886-892 (1986).

Davis et al., "The effect of density on te gastric emptying of single- and multiple-unit dosage forms", Pharmaceutical Research vol. 3, No. 4, pp. 208-213 (1986).

Devinsky et al., "New antiepileptic drugs for children: felbamate, gabapentin, lamotrigine and vigabatrin", J. Child Neurology, vol. 9, No. 1, pp. S33-S45 (1994).

DOW Chemical U.S.A. Product Information Publication, "Formulating for controlled release with methocel cellulose ethers", Oct. 5, 2007. pp. 1-34.

Dworkin et al., "Advances in neuropathic pain: diagnosis, mechanisms, and treatment recommendations", Archives of Neurology, vol. 60, pp. 1524-1534 (2003).

Eckhardt et al., "Gabapentin enhances the analgesic effect of morphine in healthy volunteers", Anesth. Analges., vol. 91, pp. 185-191 (2000).

Eldon et al., "Lack of effect of gabapentin on the pharmacokinetics of a norethindrone acetate/ethinyl estradiol-containing oral contraceptive", Neurology vol. 43 pp. A307 (1993).

Elger et al., "New antiepileptic drugs in eliptotogy", Neuropsychobiol., vol. 38, pp. 145-148 (1998).

Elwes et al., "Clinical pharmacokinetios of newer antiptileptic drugs", Clin Pharmcokinet., vol. 30, pp. 403-415 (1996).

Emilien et al., "Pharmacological management of epilepsy, mechanism of action, pharmacokinetics drug interactions, and now drug discovery possibilities", Intl. J. Clin. Pharmacol. Ther., vol. 36, pp. 181-194 (1998).

Fara, "Physiological Limitations: Gastric Emptying and Transit of Dosage Forms", *Rate Control in Drug Therapy*, L. F, Prescott, et al., eds., Churchill Livingstone, New York, (1985).

Feely, "Fortnightly review; drug treatment of epilepsy", BMJ, vol. 318, pp. 106-109 (1999).

Ferrier, "Lamotrigine and gabapentin: alternatives in the treatment of bipolar disorder", Neuropsychobiol., vol. 38, pp. 192-197 (1998).

Fischer et al., "Lack of serious toxicity following gabapentin overdose", Neurology, vol. 44, pp. 982-983 (1994).

Fix, "Oral drug delivery, small intestine and colon", *Controlled Delivery*, Mathiowitz, Ed., Wiley & Sons, Inc., pp. 699-700 (1999).

Freeman et al., "Mood stabilizer combinations: a review of safety and efficacy", Am. J. Psychiatry. vol. 155, pp. 12-21 (1998).

Fromm, "Gabapentin: discussion", Epilepsia. vol. 25, No. 5, pp. S77-S90 (1994).

Genton, "When antiepileptic drugs aggravate epiiepsy," Brain Dev., vol. 22. pp. 75-80 (2000).

Ghaemi et al., "Gabapentin treatment of the non-refractory bipolar spectrum: an open case series," J. Affective Disorders, vol. 65, pp. 167-171 (2001).

Gidal et al., "Gabapentin absorption: effect of mixing with foods of varying macronutrient composition", Ann. Pharmacother., vol. 32, pp. 405-409 (1998).

Goa et al., "Gabapentin: a review of its pharmacological properties and clinical potential in epilepsy", Drugs, vol. 46, No. 3, pp. 409-427 (1993).

Gram, "Pharmacokinetics of new antiepileptic drugs", Epilepsia, vol. 37, No. 6, pp. S12-S16 (1996).

Grundy and Foster, "The nifedipine Gastrointestinal Therapeutic System (GITS), Evaluation of Pharmaceutical, Pharmacokinetic and Pharmacological Properties", Clin. Pharmacokinet, vol. 26, pp. 435-443 (1988).

Guberman, "Monotherapy or polytherapy for epilepsy", Canadian J. Neurol. Sci., vol. 25, pp. S3-S8 (1998).

Gusler et al., "Pharmacokinetics of metformin gastric-retentive tablets in healthy volunteers", J. Clin. Pharmacol., vol. 41, No. 6, pp. 655-661 (2001).

Guttuso, Jr. et al., "Gabapentins effects on hot flashes in postmenopausal women; a randomized controlled trial", Am. College of Obstetricians and Gynecologists, vol. 101, No. 2, pp. 337-345 (2003).

Handforth, "Efficacy and tolerance of long-term, high-dose gabapentin, additional observations". Epilepsia, vol. 25, pp. 1032-1037 (1994).

Hansen, "Treatment of chronic pain with antiepileptic drugs: a new era", Southern Med. J., vol. 92, pp. 642-649 (1999).

Hou et al., "Gastric retentive dosage forms: a review", Crit Rev, Ther. Drug Carrier Syst., vol. 20, No. 6, pp. 461-497 (2003).

Irving et al., "Efficacy and safety of extended-release gabapentin for the treatment of postherpetic neuralgia", Abstract and poster presented at the 9th Int. Conf. on the Mechanisms and Treatment of Neuropathic Pain (2006).

Johnston, "GABA agonist as targets for drug development", Clin. Exp. Pharmacol. Physiol., vol. 19, pp. 73-78 (1992).

Kalviainen et al., "A double-blind, study of gabapentin in treatment of partial seizures", Epilepsia, vol. 30, pp. 661 (1989).

Kelly, "Gabapentin—antiepileptic mechanism of action". Neuropsychology, vol. 38, pp. 139-144 (1998).

Khurana et al., "Efficacy of gabapentin therapy in children with refractory partial seizures", J. Pediatrics, vol. 128, pp. 829-833 (1996).

Kushnir et al., "Analysis of gabapentin in serum and plasma by solid-phase extraction and gas chromatography—mass spectrometry for therapeutic drug monitoring", J. Anal. Toxicol., vol. 23, pp. 1-6 (1999).

Lard et al., "Use of gabapentin in the treatment of neuropathic pain", Ann. Pharmacotherapy, vol. 34, pp. 802-807 (2000).

Lederman et al., "Gabapentin as add-on therapy for refractory partial epilepsy: results of five placebo-controlled trials", Epilepsia, vol. 35, No. 5, pp. S74-S76 (1994).
Letterman et al., "Gabapentin: a review of published experience in the treatment of bi-polar disorder and other psychiatric conditions", Pharmacother., vol. 19, pp. 565-572 (1999).
Loiseau, "Treatment of concomitant illnesses in patients receiving anticonvulsants: drug interactions of clinical significance", Drug Safety, vol. 19, pp. 495-510 (1998).
Macdonald et al., "Antiepileptic drug mechanisms of action", Epilepsia, vol. 34, No. 5, pp. S1-S8 (1993).
Magnus, "Nonepileptic uses of gabapentin", Epilepsia, vol. 40, No. 6, pp. S66-S72 (1999).
Mancardi et al., "Gapapetin is effective in treating nocturnal painful tonic spasms in multiple sclerosis", Neurology, vol. 52, No. 2, pp. A134 (1999).
Mao et al., "Gabapentin in pain management", Anaesth. Analges., vol. 91, pp. 680-687 (2000).
Mathew et al., "Efficacy of gabapentin in migraine prophylaxis", Headache, vol. 41, pp. 119-128 (2001).
Mattson, "Antiepileptic drug monitoring: a reappraisal", Epilepsia, vol. 36, No. 5, pp. S22-S29 (1995).
Maurer et al., "Intestinal absorption of gabapentin in rats", Arnzeim-Forsch/Drug Res., vol. 41, pp. 104-106 (1991).
Mclean. "Gabapentin", Epilepsia, vol. 36, No. 2, pp. S73-S86 (1995).
Meldrum, "Update on the mechanism of action of antiepileptic Drugs", Epilepsia, vol. 37, Bo. 6, pp. S4-S11 (1996).
Miles et al., "Differentiating possible transport mechanisms for the intestinal absorption of gabapentin", Pharmac. Res., vol. 11, No. 1, pp. S365 (1994).
Miles et al., "Variables affecting the intestinal absorption of water soluble and insoluble antiepileptic agents", Pharmac. Res., vol. 10, No. 10, pp. S223 (1993).
Morrell, "The new antiepileptic drugs and women: fertility, reproductive health, pregnancy and fetal outcome", Epilepsia, vol. 37, No. 6, pp. S34-S44 (1996).
Morrell, "Epilepsy in women: the science of why it is special", Neurology, vol. 53, No. 1, pp. S42-S48 (1999).
Morris, "Gabepentin", Epilepsia, vol. 40. No. 5, pp. S63-S70 (1999).
Muscas et al., "Conversion From Thrice Daily to Twice Daily Administration of Gabapentin (GBP) In Partial Epilepsy: Analysis of Clinical Efficacy and Plasma Levels", Seizure, vol. 9, No. 1, pp. 47-50 (2000).
NDA 20-235 (U.S. Food and Drug Administration application No. 020235), retrieved Dec. 22, 1993.
NDA20-235 obtained via Freedom of Information Act, "Basics Pharmacokinetics Bioavailability"—optimal absorpton, dose proportionality, and sustained release formulation (study #877-076) and "general comments to the medical reviewer", retrieved Dec. 22, 1993.
NDA 20-882 (U.S. Food and Drug Administration application No. 020882), retrieved Nov. 18, 2010.
NDA 21-129 (U.S. Food and Drug Adminitstration application No. 021129), retrieved Nov. 18, 2010.
Pande et al., "Piacebo-Controlled study of gabapentin treatment of panic disorder," J. Clin. Psychopharmacol., vol. 20, pp. 467-471 (2000).
Pande et al., "Treatment of social phobia with gabapentin; a placebo-controlled study", J. Clin. Psychopharmacol., vol. 19, pp. 341-348 (1999).
Parks et al., "Practical therapeutics: drug therapy for epilepsy". Am. Family Physican vol. 80, pp. 639-648 (1994).
Patsalos et al., "Newer Antiepileptic drugs: towards an improved risk-benefit ratio," Drug Safety, vol. 11, pp. 37-67 (1994).
Perucca et al., "Antiepileptic drugs as a cause of worsening seizures", Epilepsia, vol. 39, pp. 5-17 (1998).
Perucca, "The new generation of antiepileptic drugs: advantages and disadvantages"Br. J. Clin. Psychopharmacol., vol. 42, pp. 531-543 (1996).
Piyapolrungroj et al., "Mucosal uptake of gabapentin (neurontin) vs. pregabalin in the small intestine". Pharm. Res., vol. 18, No. 8, pp. 1128-1130 (2001).

Raby, "Gabapentin therapy for cocaine cravings", Am. J. Psychiatry, vol. 157, pp. 2058-2089 (2000).
Ragucci et al., "Gabapentin-induced hypersensitivity syndrome", Clin. Neuropharmacol. , vol. 24, pp. 103-105 (2001).
RIchter et al., "Pregabalin or morphine and gabapentin for neuropathic pain", Expert Op. on Pharmacotherapy, vol. 6, No. 14, pp. 2535-2539 (2005).
Riva et al., "Pharmacokinetics interactions between antiepileptic drugs: cilnical considerations", Clin. Pharmacciktrietics, vol. 31, pp. 470-493 (1995).
Rocci et al., "Food-induced gastric retention and absorption of sustained-release precainamide", Clin. Pharmacol. Ther., vol. 42, pp. 45-49 (1987).
Rosenberg et al., "The effect of gabapentin on neuropathic pain", Clin. J. Pain, vol. 13, pp. 251-255 (1997).
Rowan et al., "Intensive monitoring and pharmacokinetics studies of gabapentin in patients with generalized spike-wave discharges", Epilepsia, vol. 30, pp. 661 (1989).
Sabers et al., "New anticonvulsants; comparative review of drug interactions and adverse effects". Drugs, vol. 60, pp. 23-33 (2000).
Salinsky et al., "Effects of chronic gabapentin and carbamazepine treatment on EEG, alertness and cognition in healthy volunteers": Epilepsia, vol. 41, No. 7, pp. 151, Abst. #2240 (2000).
Schmidt et al., "The new anticonvulsant drugs: implications for avoidance of adverse effects", Drug Safety. vol. 11, pp. 422-431 (1994).
Shovron et al., "Overview of the safety of newer antiepileptic drugs", Epilepsia, vol. 38, No. 1, pp. S45-S51 (1997).
Sindrup et al., "Efficacy of pharmacological treatments of neuropathic pain: an update and effect related to mechanism of drug action", Pain, vol. 83, pp. 389-400 (1999).
Sirkia et al., "Use of hydrophilic polymers to control drug release from press-coated oxybutynin hydrochloride tablets", S.T.P. Pharma Sciences. vol. 3. No. 6, pp. 453-458 (1993).
Sivenius et al., "Double-blind study of gabapentin in the treatment of partial seizures", Epilepsia, vol. 32, pp. 539-542 (1991).
Solaro et al., "Gabapentin is effective in treating nocturnal painful spasms in multiple sclerosis", Multiple Sclerosis, vol. 6, pp. 192-193 (2000).
Soliman et al., "Gabapentin treatment for cocaine dependence in methadone-maintained opiod-dependent patients". Drug Alcohol Depend., vol. 60, Supp. 1, Abst #S208 (2000).
Stevenson et al., "Contrasting nutrient effects on the plasma level of an amino acid-like antiepileptic agent from jejunal administration in dogs". J. Pharm. Sci., vol. 86, No. 8, pp. 953-957 (1997).
Stevenson et al., "Coloric Absorption of Antiepileptic Agents", Epilepsia, vol. 38, pp. 63-67 (1997).
Stewart et al., "A saturable transport mechanism in the intestinal absorption of gabapentin in the underlying cause of the lack of proportionality between increasing dose and drug levels in plasma", Pharmac. Res., vol. 10, pp. 276-281 (1993).
Thomson et al., "Pharmacokinetics optimization of anticonvulsant therapy", Clin. Pharmacokinet., vol. 23, pp. 216-230 (1992).
Tomson, "Therapeutic monitoring of the new antiepileptic drugs", Eur. J. Clin. Pharmacol., vol. 55, pp. 697-705 (2000).
Upton, "Mechanisms of action of new antiepileptic Drugs: rational design and serendipitous findings", Tips, vol. 15, pp. 456-463 (1994).
Vollmer, "Pharmacokinetics and metabolism of gabapentin in rat, dog and man", Arnzeim-Forsch/Drug Res., vol. 36, pp. 830-839 (1986).
Wang et al., "The simultaneous estimation of the influx and efflux blood-brain barrier permeabilities of gabapentin using a microdialysis-pharmacokinetic approach", Pharmac. Res., vol. 13, pp. 398-403 (1996).
Welling and Barbhajya, "Influence of Food and Fluid Volume on Chlorothiazide Bioavailability: Comparison of Plasma and Urinary Excretion Methods", J. Pharm. Sci., vol. 71, pp. 32-35 (1982).
Wesche et al., "A pharmacokinetic comparison of pregabalin and gabapentin", J. Pain, vol. 6, No. 3, (2005) abstract only.
Wheeler, "Gabapentin", Current Opinion in Investigational Drugs, vol. 3, No. 3, pp. 470-477 (2002).

White, "Comparative anticonvulsant and mechanistic profile of the established and newer antiepileptic drugs", Epilepsia., vol. 40, No. 5, pp. S2-S10 (1999).

Wilding et al., "Relationship Between Systemic Drug Absorption and Gastrointestinal Transit After the Simultaneous Oral Administration of Carbamazepine as a Controlled-Release System and as a Suspension of $^{15}$N-labelled Drug to Healthy Volunteers", Br. J. Clin Pharmac., vol. 32, pp. 573-579 (1991).

Wolf et al., "Gabapentin toxicity in children manifesting as behavioral changes." Epilepsia, vol. 36, pp. 1203-1205 (1996).

Wong et al., "Adverse reactions to new anticonvulsant drugs", Drug Safety, vol. 239, pp. 35-56 (2000).

Wong et al., "Clinical research: the long-term use of gabapentin, lamotrigine and vigabatrin in patients with chronic epilepsia", vol. 40, pp. 1439-1446 (1999).

Wong et al., "Disposition of gabapentin in anuric subjects on hemodialysis", J. Clin. Pharmacol., vol. 35, pp. 622-626 (1995).

Zylicz, "Painful gynecomastia: an unusual toxicity of gabapentin", Letters, vol. 20, pp. 2-3 (2000).

Beydoun et al., "Gabapentin: pharmacokinetics, efficacy, and safety", Clinical Neuropharmacology, vol. 18, No. 6. pp. 469-481 (1995).

Collins et al., "Extended release formulations of anticonvulsant medications", CNS Drugs, vol. 14, No. 3, pp. 203-212 (2000).

Deshpande et al. "Development of a novel controlled-release system for gastric retention" Pharm. Res., vol. 14, No. 6, pp. 815-819 (1997).

Feely and Davis, "Correlation of phenylpropanolamine bioavailability with gastrointestinal transit by scintigraphic monitoring of 111In-labeled hydroxypropylmethycellulose matrices", Pharmaceutical Research, vol. 6, No. 4, pp. 274-278 (1989).

Gidal et al., "Gabapentin bioavailability: effect of dose and frequency of administration in adult patients with epilepsy", Epilepsy Research, vol. 31, No. 2, pp. 91-99 (1998).

Hwang, "Gastric retentive drug-delivery systems", Critical Reviews in Therapeutic Drug Carrier Systems, vol. 15, No. 3, pp. 243-284 (1998).

Kriel et al., "Failure of absorption of gabapentin after rectal administration", Epilepsia, vol. 38, No. 11, pp. 1242-1244 (1997) Abstract only.

Lee et al., "Oral mucosa controlled delivery of LHRH by bilayer mucoadhesive polymer systems", J. Contr. Rel., vol. 19, pp. 251-261 (1995).

Leppik, "Antiepileptic drugs in development: prospects for the near future", Epilepsia, vol. 35, Suppl. 4, pp. S29-S40 (1994).

*POLYOX Water-Soluble Resins NF In Pharmacuetical Applications*, "An introduction to POLYOX water soluble resins", The Dow Chemical Company, Brochure, 12 pgs. (2004).

Rao et al., "Influence of molecular size and water solubility of the solute on its release from swelling and erosion controlled polymeric matrices", J. Conrolled Release, vol. 12, Issue 2, pp. 133-141 (1990).

Timmins et al., "Optimization and characterization of a pH-independent extended-release hydrophilic matrix tablet"., Pharmacuetical Development & Technology, vol. 2, No. 1, pp. 25-31 (1997).

Vollmer et al., "Summary of neurontin (gabapentin) clinical pharmacokinetics", Epilepsia, vol. 33, Suppl. 3, pp. 77 (1992).

Welling, "Interactions affecting drug absorption", Clin Pharmacokinet., vol. 9, No. 5, pp. 404-434 (1984).

Adelman and Adelman, "Current options for the prevention and treatment of migrane", Clin. Ther., vol. 23, No. 6, pp. 772-788 (2001).

Apicella et al., "Poly(ethylene oxide) (PEO) and differnet molecular weight PEO blends monolithic devices for drug release", Biomaterials, vol. 14, No. 2, pp. 83-90 (1993).

Babu et al., "In vitro and in vivo studies of sustained-release floating dosage forms containing salbutamol sulfate", Pharmazie, vol. 45, pp. 268-270 (1990).

Backonja et al., "Gabapentin for the treatment of painful neuropathy in patients with diabetes mellitus. A randomized controlled study", JAMA, vol. 280, No. 21, pp. 1831-1836 (1998).

Bazil and Bazil, "Recent advances in the pharmacotherapy of epilepsy", Clin. Ther., vol. 19. Issue 3, pp. 369-382 (1997).

Bolger et al., "Simulation of the nonlinear dose dependence for substrates of influx and efflux transporters in the human intestine", The AAPS Journal, vol. 11, No. 2, pp. 353-363 (2009).

"Drug delivery to the gastrointestinal tract", Hardy et al., ed., *Ellis Horwood books in biological sciences, Series in pharmaceutical technology*, Ellis Horwood Limited, Halsted Press: a division of John Wiley & Sons, New York, NY, USA, Chapter 3, pp. 37-48 (1989).

Di Trapani et al., "Gabapentin in the prophylaxis of migrane: a double-blind randomized placebo-controlled study", Clin. Ter., vol. 151, No. 3, pp. 145-148 (2000) Abstract Only.

Edgren et al., "Controlled release technology, pharmaceutical", *Kirk-Othmer encyclopedia of Chemical Technology*, John Wiley & Sons, Inc., Online ISBN: 9780471238966, DOI: 10.1002/0471238961, 24 pgs.(2000).

Ford et al., "Importance of drug type, tablet shape and added diluents on drug release kinetics from hydroxypropylmethylcellulose matrix tablets", Int'l. J. Pharmaceutics, vol. 40, pp. 223-234 (1987).

Hunt et al., "A relation between the chain length of fatty acid and the slowing of gastric emptying", J. Physiol., vol. 194, pp. 327-336 (1968).

Khosla and Davis, "The effect of tablet size on the gastric emptying of non-disintergrating tablets", Int. J. Pharm., vol. 62, pp. R9-R11 (1990).

Kim, "Drug release from compressed hydrophilic POLYOX-WSR tablets", J. Pharmaceutical Sci., vol. 84, No. 3 pp. 303-306 (1995).

Lal et al., "Clinical pharmacokinetic drug interaction studies of gabapentin enacarbil, novel transported prodrug of gabapentin, with naproxen and cimetidine", Br. J. Clin. Pharmacol, vol. 69, No. 5, pp. 498-507 (2010).

Mathew et al., "Efficacy of gabapentin in migrane prophylaxis", Headache, vol. 41, No. 2, pp. 119-128 (2001).

Mclean, "Gabapentin: chemistry, absorption, distribution, and excretion", *Antiepileptic Drugs, 4th Edition*, Levy, Mattson, and Meldrum, eds., Raven Press, Ltd., New York, NY, USA, pp. 843-849 (1995).

Papadimitriou et al., "Swelling studies on mixtures of two hydrophilic excipients", S T.P. Pharma Sciences, vol. 3, No. 3, pp. 232-236 (1993).

Park "Enzyme-digestible swelling hydrogels swelling hydrogels as platforms for long-term oral drug delivery: synthesis and characterization", Biomaterials, vol. 9, No. 5, pp. 435-441 (1988).

"Pharmaceutical Dosage Forms" *Durgin and Hanan's Pharmacy Practice for Technicians, 4th Edition*, Durgin and Hanan, eds., Delmar Cengage Learning, Clifton Park, NY, USA, Chapter 12, pp. 198-228(2008).

*Remington: The science and practice of pharmacy*, 19th Edition, Gennaro, ed., Mack Publishing Company, Easton Pennsylvania, USA, Chapter 92, pp. 1628-1629 (1995).

Rowbotham et al., "Gabapentin for the treatment of postherpetic neuralgia, A randomized control study", JAMA, vol. 280, No. 21, pp. 1837-1842 (1998).

Shalaby et al., "In vitro and in vivo studies of enzyme-digestible hydrogels for oral drug delivery", J. Controlled Release, vol. 19, pp. 131-144 (1992).

Shojaei and Berner, "Gastric retentive dosage forms", *Design of Controlled Release Drug Delivery Systems*, Li and Jasti, ed., McGraw Hill, New York. NY, USA, pp. 173-201 (2006).

Sist et al., "Experience with gabapentin for neuropathic pain in the head and neck: report of ten cases", Regional Anasthesia, vol. 22, No. 5, pp. 473-478 (1997).

"Specific delivery to the gastrointestinal tract", *Polymeric Site-specific Pharmacotherapy*, Domb, ed., John Wiley & Sons, Ltd., Chichester, West Sussex, England, pp. 282-283 (1994).

*The Pill Book*, 8th Edition, Silverman, ed., Bantam Books, New York, pp. B-C, J-K (1998).

Timmermans et al., "The cutoff size for gastric emptying of dosage forms", J. Pharm. Sci., vol. 82. No. 8, pp. 854 (1993).

Timmermans and Moes,"Factors controlling the buoyancy and gastric retention capabilities of floating matrix capsules: new data for reconsidering the controversy", J. Pharm. Sci., vol. 83, No. 1, pp. 18-24 (1994).

Tremont-Lukats et al., "Anticonvulsants for neuropathic pain syndromes: mechanisms of action and place in therapy", Drugs, vol. 60, No. 5, pp. 1029-1052 (2000).

US 8,475,813 B2

METHODS OF TREATMENT USING A GASTRIC RETAINED GABAPENTIN DOSAGE

CROSS REFERENCE TO RELATED APPLICATIONS

This application is a continuation of U.S. Ser. No. 13/270,126, filed Oct. 10, 2011, which is a divisional of U.S. Ser. No. 12/563,781, filed Sep. 21, 2009, now U.S. Pat. No. 8,119,166, which is a divisional of U.S. Ser. No. 10/903,879 filed Jul. 30, 2004, now U.S. Pat. No. 7,612,112, which is a continuation-in-part of U.S. Ser. No. 10/280,309 filed on Oct. 25, 2002, now U.S. Pat. No. 7,438,927, which claims priority under 35 U.S.C. §119(e)(1) to U.S. Provisional Application Ser. No. 60/335,248 filed Oct. 25, 2001, the disclosures of which are all incorporated herein by reference.

FIELD OF THE INVENTION

The present invention relates to the use of gabapentin in a gastric retained dosage form. More specifically, the invention relates to the use of such dosage form to treat epilepsy and other disease states.

BACKGROUND OF THE INVENTION

Gabapentin (1-(aminomethyl)cyclohexane acetic acid) is an anti-epileptic drug that is currently available in 100 mg, 300 mg and 400 mg hard shell capsule as well as 600 mg and 800 mg tablet dosage forms, with recommended dosing of 900 mg to 1800 mg total daily dose in three divided dosages. The oral bioavailability is dose-dependent, with approximately 60% bioavailability for a dose in the range of 300-400 mg, but with only 35% bioavailability for a dose of 1600 mg (Bourgeois, *Epilepsia* 36 (Suppl. 5):S1-S7 (1995); Gram, *Epilepsia* 37 (Suppl. 6):S12-S16 (1996)). The decrease in bioavailability with dose has been attributed to carrier-mediated absorption (Stewart, et al., *Pharmaceutical Research* 10(2):276-281 (1993).

In early work with rats, Vollmer, et al., *Arzneim-Forsch/Drug Research* 36(1, Nr. 5):781-892 (1986) found that the absorption site for gabapentin was the duodenum. The absorption of gabapentin occurs relatively slowly with the peak plasma concentration occurring approximately 2-6 hours after dosing (Bourgeois, supra). The elimination of gabapentin is exclusively through renal pathways (Chadwick; *The Lancet* 343:89-91 (1994); Vollmer, supra; Thomson, et al., *Clin. Pharmacokinet.* 23(3):216-230 (1992); and Riva, et al., *Clin. Pharmacokinet.* 31(6):470-493 (1996)) with reported half-lives of 5-7 hours (Chadwick, supra) and 6-7 hours (Gram, supra).

A once- or twice-daily dosage form of gabapentin would be expected to improve compliance and therefore a controlled release dosage form has some distinct advantages over the conventional immediate release formulations. In addition, a controlled release dosage form would lower the maximum plasma concentration, and this may result in reduced side effects. Since gabapentin is absorbed high in the gastrointestinal tract, by means of a saturable transport mechanism, a gastric retained dosage form is particularly beneficial for delivery of gabapentin since the dosage form would be able to keep the drug in the region of absorption and show improved bioavailability by virtue of the slower release rate that avoids saturation of the carrier mediated transport of conventional dosages.

Osmotic dosage forms have been described for delivery of gabapentin prodrugs. U.S. Pat. No. 6,683,112 to Chen et al. describes sustained release formulations that deliver gabapentin prodrugs by means of the push-pull osmotic pump system described in U.S. Pat. No. 4,612,008 to Wong et al. This system however, is not a gastric retained dosage form and would be expected to deliver the drug with poor bioavailability.

SUMMARY OF THE INVENTION

One aspect of the invention relates to a method of treating epilepsy comprising administering a therapeutically effective amount of gabapentin or a pharmaceutically acceptable salt thereof, in a gastric retained dosage fowl to a mammal in need of such treatment.

Yet another aspect of the invention relates to a method of treating neuropathic pain comprising administering a therapeutically effective amount of gabapentin or a pharmaceutically acceptable salt thereof; in a gastric retained dosage form to a mammal in need of such treatment.

Still another aspect of the invention relates to an improved method of administering a therapeutically effective amount of gabapentin to a patient in need thereof; the improvement comprising administering gabapentin or a pharmaceutically acceptable salt thereof; in a gastric retained dosage form.

Yet another aspect of the invention pertains to an extended release oral drug dosage form for releasing gabapentin into the stomach, duodenum and small intestine of the mammal, comprising a core comprising at least 800 mg of gabapentin, surrounded by a semipermeable membrane or coating, which can be porous or non-porous.

DETAILED DESCRIPTION OF THE INVENTION

Figure 1:
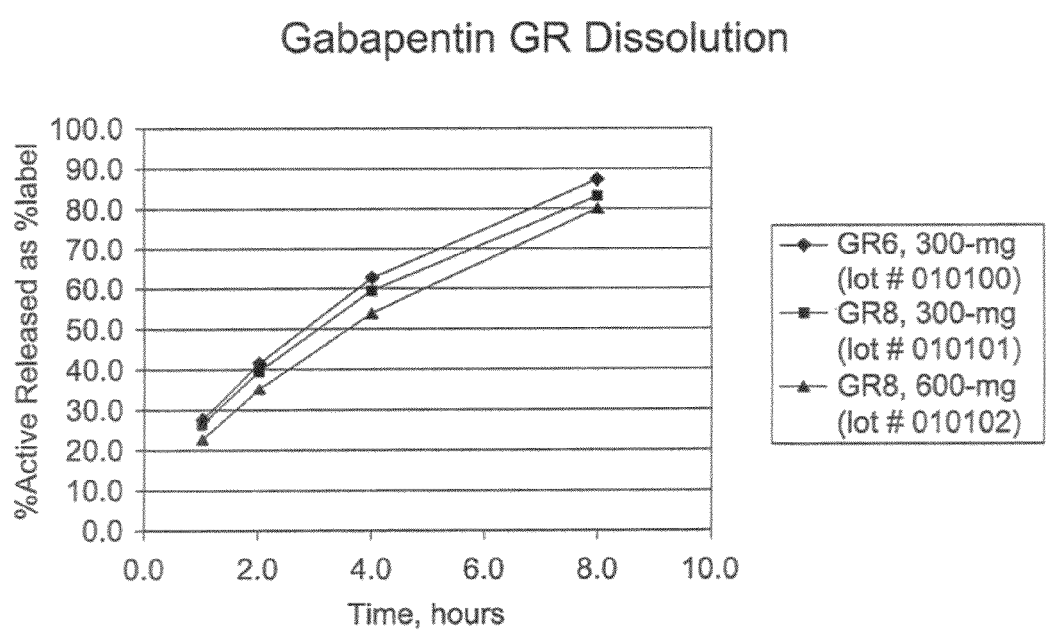
FIG. 1 illustrates the dissolution profiles for three GR™ formulations.

The invention relates to a method of treating a disease state, such as epilepsy, by administering gabapentin in a once- or twice-daily gastric retained dosage form. The gastric retained dosage form is particularly beneficial for delivery of gabapentin due to its prolonged transit in the upper gastrointestinal tract, which allows the drug to be absorbed adequately in the preferred region of absorption. In addition, a gastric retained dosage form increases the $t_{max}$, and allows for a smoother, more prolonged anti-spasmolytic effect. This dosage form also lowers the $C_{max}$ and may result in reduced incidence and/or severity of CNS side effects of the drug, such as somnolence, ataxia, fatigue and dizziness.

A. Method of Treatment

The instant invention is a method of treating a disease state comprising administering a therapeutically effective amount of gabapentin, or a pharmaceutically acceptable salt thereof, once- or twice-daily in a gastric retained dosage form to a mammal in need of such treatment. As used herein, the term "treating" covers treating the specified disease in a mammal, particularly a human, and includes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease.

One embodiment of the invention relates to an improved method of administering a therapeutically effective amount of gabapentin to a patient in need thereof, the improvement comprising administering gabapentin or a pharmaceutically acceptable salt thereof, in a gastric retained dosage form.

Other embodiments of the invention relate to methods of treating specific disease states comprising administering a therapeutically effective amount of gabapentin or a pharmaceutically acceptable salt thereof, in a gastric retained dosage form to a mammal in need of such treatment. Such methods find utility in treating numerous disease states that are currently being treated with conventional immediate release formulations of gabapentin and include, by way of illustration and not limitation, epilepsy; neuropathic pain; psychiatric disorders such as bipolar disorder and panic disorder; movement disorders such as restless leg syndrome, periodic movement disorder of sleep, essential tremor and acquired nystagmus; and prophylaxis of migraine headaches.

The invention also contemplates administering one or more additional therapeutic agents with the gabapentin treatment. The selection of these additional therapeutic agents will depend upon the specific disease state being treated, and are described in detail below.

B. Active Ingredient

The active ingredient in the method of the invention is gabapentin. Gabapentin is preferably used in the free amphoteric form. Pharmaceutically acceptable salt forms that retain the biological effectiveness and properties of gabapentin and are not biologically or otherwise undesirable can also be used and may show superior bioavailability. As used herein, the term "gabapentin" is intended to include the agent itself, as well as its pharmaceutically acceptable salts.

Pharmaceutically acceptable salts may be amphoteric and may be present in the form of internal salts. Gabapentin may form acid addition salts and salts with bases. Exemplary acids that can be used to form such salts include, by way of example and not limitation, mineral acids such as hydrochloric, hydrobromic, sulfuric or phosphoric acid or organic acids such as organic sulfonic acids and organic carboxylic acids. Salts formed with inorganic bases include, for example, the sodium, potassium, lithium, ammonium, calcium, and magnesium salts. Salts derived from organic bases include, for example, the salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethyl aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, fumarate, maleate, succinate, acetate and oxalate.

C. Additional Therapeutic Agents

The methods of the invention also contemplate the addition of one or more therapeutic agents with the gabapentin treatment.

For those embodiments of the invention where the gabapentin gastric retained dosage form is administered to treat epilepsy, such additional therapeutic agents can be other antiepileptics or anticonvulsants, which include, by way of illustration and not limitation, hydantoins, iminostilbenes, valproates, phenyltriazines, barbiturates, deoxybarbiturates, benzodiazepines and carbamates. Such additional agents are preferably hydantoins, iminostilbenes, valproates or phenyltriazines.

The following examples of compounds within each of these classes is intended to be illustrative and not limiting in any manner. Examples of suitable hydantoin anticonvulsants include ethotoin, fosphenyloin, mephenyloin, and, preferably, phenyloin. An examples of a suitable iminostilbene is carbamazepine. Examples of suitable valproates include valprioic acid and sodium valproate. An exemplary suitable phenyltriazine is lamotrigene. A suitable barbiturate is phenobarbital and an exemplary deoxybarbiturate is primidone. An example of a suitable benzodiazepine is clorazepate. A suitable carbamate is felbamate.

For those embodiments of the invention where the gabapentin gastric retained dosage form is administered to treat neuropathic pain, such additional therapeutic agents can be selected from the group consisting of other anticonvulsants, tricyclic antidepressants, levadopa, and opioids.

The following examples of compounds within each of these classes is intended to be illustrative and not limiting in any manner. Examples of suitable anticonvulsants include carbamazepine, phenyloin and lamotrigine. Suitable tricyclic antidepressants include amitriptyline, imipramine, clomipramine and desipramine. Examples of suitable opioids include oxycodone and tramadol.

For those embodiments of the invention where the gabapentin gastric retained dosage form is administered to treat psychiatric disorders, such additional therapeutic agents can be selected from the group consisting of lithium, carbamazepine, valproate, trifluoperazine, clonazepam, risperidone, lorazepam, venlafaxine, clozapine, olanzapine, benzodiazepines, neuroleptics, tricyclic antidepressants, selective serotonin reuptake inhibitor (SSRI's), buprupion, and nefadone.

For those embodiments of the invention where the gabapentin gastric retained dosage form is administered to treat bipolar disorder, such additional therapeutic agents can be selected from the group consisting of lithium, carbamazepine, valproate, trifluoperazine, clonazepam, risperidone, lorazepam, venlafaxine, clozapine, olanzapine, benzodiazepines, and neuroleptics.

For those embodiments of the invention where the gabapentin gastric retained dosage form is administered to treat depression, such additional therapeutic agents can be selected from the group consisting of tri-cyclic anti-depressants, SSRI's, bupropion, venlaxatine, and nefadone.

For those embodiments of the invention where the gabapentin gastric retained dosage form is administered to treat manic disorders, such additional therapeutic agents can be selected from the group consisting of diazepam, and oxazepam.

For those embodiments of the invention where the gabapentin gastric retained dosage form is administered to treat movement disorders, such additional therapeutic agents can be selected from the group consisting of benzodiazepines, dopaminergic agents, and opiates, particularly levodopa/carbidopa and clonazepam.

For those embodiments of the invention where the gabapentin gastric retained dosage form is administered for prophylactic treatment of migraine headaches, such additional therapeutic agents can be selected from the group consisting of tricyclic antidepressants (amitriptyline, doxepin, imipramine, maprotiline, protriptyline, desipramine), SSRI (fluoxetine), triptan (sumatriptan, etc.), and ergotamine.

D. Dosage

In general, the term "therapeutically effective amount" refers to that amount which is sufficient to effect treatment, when administered to a mammal in need of such treatment. The therapeutically effective amount will vary depending on the subject being treated, the severity of the disease state and the manner of administration, and may be determined routinely by one of ordinary skill in the art.

In particular, for use in the treatment of epilepsy or neuropathic pain with a gastric retained dosage form, gabapentin may be used at doses appropriate for treating epilepsy or neuropathic pain with immediate release dosage forms. However, the gastric retained dosage form is designed to provide for bioavailability of gabapentin at a level greater than or equal to 80% (>80%) relative to an equal dose of an immediate release dosage form. Typically, the method of the invention will involve administering gabapentin on a once- or twice-daily basis for as long as the condition persists.

An effective dosage of gabapentin for the treatment of epilepsy is typically in the range of about 300-3600 mg/day, typically about 900-2400 mg/day, more typically about 900-1800 mg/day.

An effective dosage of gabapentin for the treatment of neuropathic pain is typically in the range of about 100-4800 mg/day, typically about 300-3600 mg/day, more typically about 900-2400 mg/day.

An effective dosage of gabapentin for the treatment of psychiatric disorders is typically in the range of about 100-4800 mg/day, more typically about 900-3600 mg/day.

An effective dosage of gabapentin for the treatment of movement disorders is typically in the range of about 100-4000 mg/day, typically about 200-2700 mg/day, more typically about 500-2700 mg/day.

An effective dosage of gabapentin for the prophylactic treatment of migraine headaches is typically in the range of about 200-4000 mg/day, typically about 500-3600 mg/day, more typically about 900-2400 mg/day.

E. Dosage Regimen

The methods of the invention provide a once- or twice-daily dose of the gabapentin gastric retained dosage form. The dosage can be administered at any time, but it is preferred that the dosage is administered at the same approximate time each day and in approximately 12 hour intervals for the duration of treatment. In addition, it is preferred that the gastric retained dosage form be taken with food, for example with the morning or evening meals.

Accordingly, in one embodiment of the invention, gabapentin is administered once-daily, for example, in the morning (e.g., upon rising or with the morning meal) or in the evening (e.g., with the evening meal or near bedtime).

In another embodiment of the invention, gabapentin is administered twice-daily, for example, with the first dose being in the morning (e.g., upon rising or with the morning meal) and the second dose being in the evening (e.g., with the evening meal or near bedtime).

In another aspect of the invention, the method of administering a therapeutically effective amount of gabapentin in a gastric retained dosage form further includes administering one or more additional therapeutic agents.

The additional therapeutic agents can be administered at the same time or at a different time than the administration of gabapentin, and will depend upon the nature of the disease being treated as well as the agent itself. For example, when the additional agent is another anti-epileptic, a twice-daily dose is sufficient and it may be administered at the same time or at a different time than gabapentin. For purposes of facilitating patient compliance, administration of any of the aforementioned additional agents at the same time is preferred.

F. Dosage Form

There are several drug delivery systems that are suitable for use in delivering gabapentin in the method of the invention as they are particularly tailored to be gastric-retained dosages, such as the swellable bilayer described by Franz, et al., U.S. Pat. No. 5,232,704; the multi-layer tablet with a band described by Wong, et al., U.S. Pat. No. 6,120,803; the membrane sac and gas generating agent described in Sinnreich, U.S. Pat. No. 4,996,058; the swellable, hydrophilic polymer system described in Shell, et al., U.S. Pat. No. 5,972,389 and Shell, et al., WO 9855107; all of which are incorporated herein by reference.

Of particular interest are gastric retained dosage forms that contain hydrophilic polymers that swell to a size such that the dosage form is retained in the fed mode. For example, the gastric retained dosage form can contain polymers with a high swelling capacity such as polyethylene oxide, hydroxyethylcellulose and hydroxypropylmethylcellulose. The polymers are preferably of a moderate to high molecular weight ($4 \times 10^3$ to greater that $10^7$) to enhance swelling and provide control of the release of gabapentin. In one embodiment of the invention, a hydroxypropylmethylcellulose polymer of such molecular weight is utilized so that the viscosity of a 1% aqueous solution is about 4000 cps to greater than 100,000 cps. An example of suitable polyethylene oxide polymers are those having molecular weights (viscosity average) on the order of 2-7 million. A typical dosage form should swell to approximately 115% of its original volume within one hour after administration, and at a later time should swell to a volume that is 130% or more of the original volume. Fillers, hinders, lubricants and other additives may also be included in the gastric retained dosage form, such as are well known to those of skill in the art.

A typical dosage form would provide for a drug delivery profile such that gabapentin both on an in vivo and in vitro basis, is delivered for at least 5 hours, and typically over a time period of about 8-10 hours. In order to provide for sustained delivery, it is preferable that at least 40 wt % of gabapentin is retained in the dosage form after 1 hour, i.e., no more than 60 wt % of the drug is administered in the first hour. In addition, it may be desired to utilize a dosage form that provides for substantially all of the gabapentin to be delivered over the intended duration, which is typically about 6-12 hours, where substantially all is taken to mean at least about 85 wt % of the gabapentin is administered.

In one embodiment of the invention, the gastric retained dosage form of gabapentin is a capsule dosage form that allows for the extended release of gabapentin in the stomach and comprises: (a) at least one component that expands on contact with gastric juice and contains an agent capable of releasing carbon dioxide or nitrogen, gabapentin or a pharmaceutically acceptable salt thereof; (b) at least one hydrophilic membrane in the form of a sachet which contains component (a), expands by inflation, floats on the aqueous phase in the stomach and is permeable to gastric juice and; (c) capsule dosage form which contains components (a) and (b) and which disintegrates without delay in the stomach under the action of gastric juice. Component (a) may also contain a pharmaceutically acceptable hydrophilic swelling agent such as lower alkyl ethers of cellulose, starches, water-soluble aliphatic or cyclic poly-N-vinylamides, polyvinyl alcohols, polyacrylates, polymethacrylates, polyethylene glycols and mixtures thereof, as well as other materials used in the manufacture of pharmaceutical dosage forms. Further details regarding an example of this type of dosage form can be found in Sinnreich, U.S. Pat. No. 4,996,058.

In another embodiment of the invention, the gastric retained dosage form of gabapentin is an extended release oral drug dosage form for releasing gabapentin into the stomach, duodenum and small intestine of a patient, and comprises: a single or a plurality of solid particles consisting of gabapentin or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii)

gradually the gabapentin diffuses or the polymer erodes over a time period of hours, where the diffusion or erosion commences upon contact with the gastric fluid; and (iii) releases gabapentin to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107.

In yet another embodiment, a bi-layer tablet releases gabapentin to the upper gastrointestinal tract from an active containing layer, while the other layer is a swelling or floating layer. Details of this dosage may be found in Franz, et al., U.S. Pat. No. 5,232,704. This dosage form may be surrounded by a band of insoluble material as described by Wong, et al., U.S. Pat. No. 6,120,803.

Another embodiment of the invention uses a gastric retained swellable, sustained-release tablet having a matrix comprised of poly(ethylene oxide) and hydroxypropylmethylcellulose. This dosage form is illustrated in Example 1 and further details may be found in Gusler, et al., U.S. Patent Application Publication No. 20030104053.

Yet another embodiment of the invention relates to a dosage form that is formulated to have a large enough size so as to provide for prolonged transit in the upper gastrointestinal tract. Such tablets would contain at least 800 mg of gabapentin, typically 800-1600 mg. Typically such a dosage form will be a film coated dosage form or a capsule dosage form that allows for the controlled and extended release of gabapentin in the stomach. In a preferred embodiment, the dosage form is a drug-containing core surrounded by a controlled release film coating that provides for controlled or sustained drug release, i.e., continuous diffusion of drug from the core into the upper gastrointestinal tract.

Numerous materials useful for manufacturing these large-sized dosage forms are described in *Remington: The Science and Practice of Pharmacy*, 20*th* edition (Lippincott Williams & Wilkins, 2000) and Ansel et al., *Pharmaceutical Dosage Forms and Drug Delivery Systems*, 6*th* Ed. (Media, Pa.: Williams & Wilkins, 1995). Along with gabapentin, the core may contain pharmaceutically acceptable additives or excipients to facilitate manufacturing. These include binders (e.g., ethyl cellulose, gelatin, gums, polyethylene glycol, polyvinylpyrrolidone, polyvinylalcohol, starch, sugars, waxes), coloring agents, diluents (e.g., calcium sulfate, cellulose, dicalcium phosphate, kaolin, lactose, mannitol, microcrystalline cellulose, sodium chloride, sorbitol, starch, sucrose), flavoring agents, glidants (e.g., colloidal silicon dioxide, talc), and lubricants (e.g., calcium stearate, glyceryl behenate, hydrogenated vegetable oils, magnesium stearate, polyethylene glycol, sodium stearyl fumarate, stearic acid, stearyl behenate, talc). The core may also contain pharmaceutically acceptable additives or excipients that serve to provide desirable physical characteristics to the dosage form. These include sweeteners, polymers, waxes and solubility-retarding materials. These dosage forms can be made by techniques that are well established in the art, including wet granulation, fluid-bed granulation, dry granulation, direct compression, and so forth.

The controlled release film coating can also be applied by techniques that are well established in the art, for example, by dissolving the material in an appropriate solvent such as acetone or methylene chloride and is then applying the coating to the dosage form core by molding, air spraying, dipping or brushing a solvent-based solution of the material onto the core. Materials suitable for use in controlled release film coatings include by way of illustration, and not limitation, mixtures of waxes such as beeswax and carnuba wax, shellac and zein, celluloses such as ethyl cellulose, acrylic resins, cellulose acetates including diacetates and triacetates and other cellulose esters, and silicone elastomers. Additional examples are set forth below.

Of particular interest are controlled release film coating materials that can form a semipermeable membrane or coating, which can be porous or non-porous, and which are permeable to external fluid, and substantially impermeable to the unsolubilized drug contained within the core. Typically, external fluids are aqueous fluids or biological fluids in the environment of use, such as the upper gastrointestinal tract. External fluid passes through the semipermeable membrane into the core, where it solubilizes the drug. The solubilized drug then moves from the core through the membrane into the gastrointestinal tract.

After application of the controlled release film coating to the core, a drying step is required and then, a suitable exit means for the gabapentin must be formed through the semipermeable membrane. Depending on the properties of the gabapentin and other ingredients within the internal compartment and the desired release rate for the dosage form, one or more orifices for gabapentin delivery can be formed through the membrane by mechanical drilling, laser drilling, or the like. The orifice(s) may range in size from a single large orifice containing substantially an entire surface of the dosage form to one or more small orifices selectively located on the surface of the semipermeable membrane. One specific embodiment of a semipermeable membrane-coated core, is the elementary osmotic pump. The membrane is provided with one or more delivery orifices, e.g., pierced with a laser to create one or more delivery orifices. Fluid passing through the membrane into the core, generates an osmotic pressure that serves to "pump" the solubilized dug through the delivery orifice(s). See for example, U.S. Pat. No. 3,845,770 to Theeuwes et al. and U.S. Pat. No. 3,977,404 to Theeuwes.

Representative of compositions of matter that can be released from the device and can function as a solute are without limitation those compositions soluble in aqueous type fluids such as tear fluid, tissue juices, water; organic solvents and the like. The expression "composition of matter" as used in this disclosure is meant to include the terms product, active agent, beneficial agent and the like, and these terms are deemed as functionally equivalent for the present invention. The composition can be a drug, nutrient, plant growth regulator, biocide, insecticide, pesticide, germicide, attractants, and the like. These compositions are osmotically effective as solutes since they can generate a solvent concentration gradient between the exterior medium and the medium inside the device. These compositions include organic and inorganic compounds such as ephedrine hydrochloride, ephedrine sulfate, hydroxyamphetamine, isoproternol hydrochloride, carbachol, pilocarpine hydrochloride, pilocarpine nitrate, demecarium bromide, echothrophate iodide, physostigmine salicylate, propranolol hydrochloride, homatropine hydrochloride, homatropine methylbromide, methscopolamine nitrate, alverine citrate, chlorphenoxamine, hydrochloride, calcium pantothenate and the like. Additional compositions that can be administered are those that produce a physiologically or pharmacalogically useful effect at a point in near relation to the delivery device, or compositions that will produce a physiological or pharmacological response at a site remote from the point of release from the device include drugs generically known as, without limitation, hypnotics, sedatives, psychic energizers, tranquilizers, anticonvulsants, muscle relaxants, analgesics, anti-inflammatory, anesthetics, anti-spasmodics, anti-ulcer agents, anti-microbials, hormonal agents, cardiovascular agents, diuretics, neoplastic agents, and the like.

The composition, drug or the like can also be in various forms, such as uncharged molecules, components of molecular complexes, pharmacologically acceptable salts such as hydrochloride, hydrobromide, sulfate, phosphate, nitrate, borate, acetate, maleate, tartrate, salicylate and the like. For acidic drugs, salts of metals, amines, or organic cations, for example quaternary ammonium can be employed. Furthermore, simple derivatives of the drug such as esters, ethers, amides and the like which have solubility characteristics are suitable for the purpose of the invention. Also, a product or drug that is water insoluble can be used in a form that is a water soluble derivative thereof to effectively serve as a solute, and on its release from the device it is converted by enzymes, hydrolyzed by body pH, or other metabolic processes to the original form or to a biologically active form. Additionally, the drug formulation can have various art known forms such as solution, dispersion, paste, cream, particle, granule, tablet, emulsions, suspensions, powders and the like. Various osmotically effective solutes including organic and inorganic compounds are advantageously used when it is desired to release a composition, product, drug or the like having limited solubility from the device. The term "limited solubility" as used herein means that the compound has a solubility of about less than 1% by weight in the external fluid, that is, the ratio of the weight of the compound in solution to the weight of the water of that solution is less than 1 percent. The term includes low, slightly and moderate solubility of the composition in the field. The osmotically effective compounds or solutes confined in the device are a substantial motive force of the device and they exhibit an osmotic pressure gradient against an external fluid across the membrane while the membrane is substantially impermeable to the passage of the osmotically effective solute to prevent loss thereof through the membrane. The solutes are conveniently used by dispensing or homogenously or heterogenously mixing a solute or a mixture of solutes with the composition, active agent, product or the like either before they are charged into the compartment or by self mixing after charging a solute and composition into the compartment. In operation, these solutes osmotically attract fluid into the device to produce a solution of the solute which is released from the device concomitantly transporting therewith undissolved and dissolved composition, product, drug or the like.

Various osmotically effective solutes include compounds such as magnesium sulfate, magnesium chloride, sodium chloride, lithium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, mixtures thereof and the like. The solid solute, present initially in excess, can be in any suitable physical form such as particles, crystals, pellets, tablets, strips, film, granules and the like.

Additionally, the composition and composition solute can be used in a mixed form by mixing the composition or product with a binder. The product in powdered, granular, piece and the like form, is homogenously or heterogenously dispersed in the binder which binder is water soluble or water insoluble but will release the product on contact with water. Typical water soluble binders include polyethylene glycol, gelatin, agar, carboxycellulose, ethylmethylcellulose, polyvinyl alcohol, polyvinylpyrrolidone, water soluble starch derivatives and the like. Typical water insoluble binders that can comprise about 1 to 50 percent of the composition include cellulose acetate, polyurethane, epoxides, and other insoluble binders that permit the free movement of water into the pores of the structure to transport the product from the binder.

The amount of composition present in the device, whether soluble, a derivitized soluble form thereof, is generally non-limited and it is an amount larger than or equal to the amount of the composition that is necessary to osmotically operate the device and on its release from the device is effective for bringing about the product's desired effect. Since the invention contemplates a variety of devices of various sizes and shapes, for a variety of uses, there is no critical upper limit on the amount of product incorporated in the device. The lower limit will depend on osmotic activity, the span of the release of the product and the activity of the product. Generally, the device will contain about 0.01 percent to 90 percent or higher of a product or a mixture of product and solute based on the weight of the product or product solute to the volume of the device, and the like. Typically, the device can be of such size and shape to release 0.01 cc to 5 cc or higher of product contained in the fluid per hour, day or longer, such as 1 cc to 10 cc of product solution for 1 to 10 days, and the like.

An osmotic delivery device can be manufactured with a first osmotic composition and a second osmotic composition mutually housed in cooperative relationship in the compartment of the device. The compartment is formed by a wall semipermeable comprising a material that does not adversely affect the beneficial agent, osmagent, osmopolymer, and the like. The semipermeable wall is permeable to the passage of an external fluid such as water and biological fluids, and it is substantially impermeable to the passage of agents, osmagents, osmopolymers, and the like. The wall is formed of a material that does not adversely affect an animal, or host, or the components comprising the device, and the selectively semipermeable materials used for forming the wall are non-erodible and they are insoluble in fluids. Typical materials for forming the wall are in one embodiment cellulose esters, cellulose ethers and cellulose ester-ethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, moni, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioclanoate, cellulose dipentale, co-esters of cellulose such as cellulose acetate butyrate and cellulose acetate propionate, and the like.

Additional semipermeable polymers include cellulose acetaldehyde dimethyl acetate, cellulose acetate ethyl carbamate, cellulose acetate methyl carbamate, cellulose acetate dimethyl aminoacetate, semipermeable polyamides, semipermeable polyurethanes, semipermeable sulfonated polystyrenes, semipermeable cross-linked selectively polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable lightly cross-linked polystyrene derivatives; semipermeable crosslinked poly(sodium styrene sulfonate); semipermeable cross-linked poly(vinylbenzyltrimethyl amonium chloride); semipermeable polymers exhibiting a fluid permeability of $10.^{-5}$ to $10.^{-1}$ (cc.mil/cm.$^2$.hr.atm) expressed per atmosphere $10.^{-8}$ of hydrostatic or osmotic pressure difference across the semipermeable wall. The polymers are known to the art in U.S. Pat. Nos. 3,845,770; 3,916,899; and 4,160,020; and in Handbook of Common Polymers by Scott, J. R. and Roff, W. J., 1971, published by CRC Press, Cleveland, Ohio.

The laminated wall comprising a semipermeable lamina and a microporous lamina are in laminar arrangement and they act in concert to form an integral laminated wall that maintains its physical and chemical integrity and does not separate into the original lamina throughout the operative agent release history of the osmotic device. The semipermeable lamina is made from the semipermeable polymeric materials presented above, the semipermeable homopolymers, the semipermeable copolymers, and the like.

Microporous lamina suitable for manufacturing the laminated osmotic device generally comprises preformed microporous polymeric materials, and polymeric materials that can form a microporous lamina in the environment of use. The microporous materials in both embodiments are laminated to a semipermeable lamina to form the laminated wall. The preformed materials suitable for forming the microporous lamina area essentially inert, they maintain their physical and chemical integrity during the period of agent release and they can be described generically as having a sponge like appearance that provides a supporting structure for a semipermeable lamina and also provides a supporting structure for microscopic sized interconnected pores or voids. The materials can be isotropic wherein the structure is homogeneous throughout a cross sectional area, or they can be anisotropic wherein the structure is non-homogeneous throughout a cross sectional area. The pores can be continuous pores that have an opening on both faces of microporous lamina, pores interconnected through totuous paths of regular and irregular shapes, including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and the number of pores.

Microporous materials having a preformed structure are commercially available and they can be made by art known methods. The microporous materials can be made by etching, nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte process. Process for repairing microporous materials are described in Synthetic Polymer Membranes, by R. E. Kesting, Chapters 4 and 5, 1971, published by McGraw Hill, Inc.; chemical Reviews, Ultrafiltration, Vol. 18, pp 373 to 455, 1934; Polymer Eng. and Sci., Vol. 11. No. 4, pp 284-288, 1971; J. Appl. Poly. Sci., Vol. 15, pp 811-829, 1971; and in U.S. Pat. Nos. 3,565,259; 3,615,024; 3,751,536; 3,801,692; 3,852,224, and 3,849,528.

Microporous materials useful for making the lamina include microporous polycarbonates comprised of linear polyesters of carbonic acid in which carbonate groups recur in the polymer chain; microporous materials prepared by the phosgenation of a dihydroxyl aromatic, such as bisphenol A; microporous poly(vinyl chloride); microporous polyamides such as polyhexamethylene adipamide; microporous modacrylic copolymers including those formed from poly (vinylchloride) 60% and acrylonitrile; styrene acrylic and its copolymers; porous polysulfones characterized by diphenylene sulfone groups in a linear chain thereof; halogenated poly(vinylidene); polychloroethers; acetal polymers; polyesters prepared by esterification of a dicarboxylic acid or anhydride with an alkylene polyol; poly(alkylenesulfides); phenolic polyesters; microporous poly(saccharides); microporous poly(saccharides) having substituted and unsubstituted anhydroglucose units exhibiting an increased permeability to the passage of water and biological fluids than a nonporous semipermeable lamina; asymmetric porous polymers; cross-linked olefin polymers; hydrophobic or hydrophilic microporous homopolymers, copolymers or interpolymers having a reduced bulk density; and materials described in U.S. Pat. Nos. 3,597,752; 3,643,178; 3,654,066; 3,709,774; 3,718,532; 3,803,061; 3,852,224; 3,853,601; and 3,852,388; in British Patent No. 1,126,849, and in Chem. Abst., 1969, Vol. 71 4274F, 22572F, 22573F.

Additional microporous materials include microporous poly(urethanes); microporous cross-linked, chain extended poly(urethanes); microporous poly(urethanes) in U.S. Pat. No. 3,524,753; microporous poly(imides); microporous poly (benzimidazoles); regenerated microporous proteins; semisolid cross-linked microporous poly(vinylpyrrolidone); microporous materials prepared by diffusion of multivalent cations into polyelectrolyte sols as in U.S. Pat. No. 3,565,259; anisotropic microporous materials of ionically associated polyelectrolytes; porous polymers formed by the coprecipitation of a polycation and a polyanion as described in U.S. Pat. Nos. 3,276,589; 3,541,055; 3,541,066 and 3,546,142; derivatives of poly(styrene), such as microporous poly(sodium styrenesulfonate) and microporous poly(vinyl benzyltrimethyl-ammonium chloride); the microporous materials disclosed in U.S. Pat. Nos. 3,615,024; and 3,646,178 and 3,852,224.

Further, the micropore forming material used for the purpose of the invention includes the embodiment wherein the microporous lamina is formed in situ by a pore former being removed by dissolving or leaching it to form the microporous lamina during the operation of the system. The pore former can be a solid or a liquid. The term liquid, for this invention, embraces semi-solids and viscous fluids. The pore formers can be inorganic or organic. The pore formers suitable for the invention include pore formers that can be extracted without any chemical change in the polymer. The pore forming solids have a size of about 0.1 to 200 micrometers and they include alkali metal salts such as sodium chloride, sodium bromide, potassium chloride, potassium sulfate, potassium phosphate, sodium benzoate, sodium acetate, sodium citrate, potassium nitrate, and the like. The alkali earth metal salts include calcium phosphate, calcium nitrate, and the like. The transition metal salts include ferric chloride, ferrous sulfate, zinc sulfate, cupric chloride, manganese, fluoride, manganese fluorosilicate, and the like. The pore formers include organic compounds such as polysaccharides. The polysaccharides include the sugars: succrose, glucose, fructose, mannitol, mannose, galactose, aldohexose, altrose, talose, sorbitol, lactose, monosaccharides and disaccharides. Also, organic aliphatic and aromatic oils and solids, including diols and polyols, as exemplified by polyhydric alcohols, poly (alkylene glycols), polyglycols, alkylene glycols, poly(.alpha.-.omega.)-alkylenediols esters or alkylene glycols and the like; water soluble cellulosic polymers such as hydroxyloweralkyl cellulose, hydroxypropyl methylcellulose, methyl cellulose, methylethyl cellulose, hydroxyethyl cellulose and the like; water soluble polymers such as polyvinylpyrrolidone, sodium carboxymethylcellulose and the like. The poreformers are nontoxic and on their removal from the lamina channels are formed through the lamina. In a preferred embodiment the non-toxic, poreforming agents are selected from the group consisting of inorganic and organic salts, carbohydrates, polyalkylene glycols, poly(.alpha.-.omega.)-alkylene-diols, esters of alkylene glycols, glycols and water soluble polymers used for forming a microporous lamina in a biological environment. Generally, for the purpose of this invention, when the polymer forming the lamina contains more than 15% by weight of a poreformer, the polymer is a precursor microporous lamina that on removing the poreformer yields a lamina which is substantially microporous.

The osmotically effective compounds that can be used for the purpose of this invention include inorganic and organic compounds that exhibit an osmotic pressure gradient across the semipermeable wall, or across a semipermeable microporous laminated wall, against an external fluid. The osmotically effective compounds, along with the osmopolymers, imbibe fluid into the osmotic device thereby making available in situ fluid for imbibition by an osmopolymer to enhance its expansion, and/or for forming a solution or suspension containing a beneficial agent for its delivery through the passageway from the osmotic device. The osmotically effective compounds are known also as osmotically effective solutes, or osmagents. The osmotically effective compounds are used by mixing them with a beneficial agent and osmopolymer for forming a solution, or suspension containing the beneficial agent that is osmotically delivered from the device. The expression limited solubility as used herein means the agent has a solubility of about less then 5% by weight in the aqueous fluid present in the environment. The osmotic solutes are used by homogeneously or heterogeneously mixing the solute with the agent or osmopolymer and then charging them into the reservoir. The solutes and osmopolymers attract fluid into the reservoir producing a solution of solute in a gel which is delivered from the system concomitantly transporting undissolved and dissolved beneficial agent to the exterior of the system. Osmotically effective solutes used for the former purpose include magnesium sulfate, magnesium chloride, potassium sulfate, sodium sulfate, lithium sulfate, potassium acid phosphate, d-mannitol, urea, inositol, magnesium succinate, tartaric acid, carbohydrates such as raffinose, sucrose, glucose, .alpha.-d-lactose monohydrate, and mixtures thereof. The amount of osmagent in the compartment will generally be from 0.01% to 30% or higher in the first composition, and usually from 0.01% to 40% or higher in the second composition.

The osmotic solute is initially present in excess and it can be in any physical form that is compatible with the beneficial agent, the osmagent, and osmopolymer. The osmotic pressure of saturated solutions of various osmotically effective compounds and for mixtures of compounds at 37.degree. C., in water, is listed in Table 1. In the table, the osmotic pressure .pi., is in atmospheres, atm. The osmotic pressure is measured in a commercially available osmometer that measures the vapor pressure difference between pure water and the solution to be analyzed and, according to standard thermodynamic principles, the vapor pressure ratio is converted into osmotic pressure difference. In Table 1, osmotic pressures of from 20 atm to 500 atm are set forth. Of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by the Hewlett Packard Co., Avondale, Pa.

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Manitol-Sucrose | 170 |
| Dextrose | 82 |
| Potassium Sulfate | 39 |
| Mannitol | 38 |
| Sodium Phosphate Tribasic 12H$_2$O | 36 |
| Sodium Phosphate Dibasic 7H$_2$O | 31 |
| Sodium Phosphate Dibasic 12H$_2$O | 31 |
| Sodium Phosphate Dibasic Anhydrous | 29 |
| Sodium Phosphate Monobasic H$_2$O | 28 |

The osmopolymers suitable for forming the first osmotic composition, and also suitable for forming the second osmotic composition, are osmopolymers that exhibit fluid imbibition properties. The osmopolymers are swellable, hydrophilic polymers which osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncrosslinked or cross-linked. The swellable, hydrophilic polymers are in one presently preferred embodiment lightly cross-linked, such cross-links being formed by covalent or ionic bonds. The osmopolymers can be of plant, animal or synthetic origin. The osmopolymers are hydrophilic polymers. Hydrophilic polymers suitable for the present purpose include poly (hydroxyalkyl methacrylate) having a molecular weight of from 30,000 to 5,000,000; polyvinylpyrrolidone) having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer reduced by forming a dispersion of finely divided copolymer of maleic anhydride with styrene, ethylene, propylene, butylene or isobutylene cross-linked with from 0.001 to about 0.5 moles of polyunsaturated cross-linking agent per mole of maleic anhydride in the copolymer; water swellable polymers of N-vinyl lactams, and the like.

Other osmopolymers include polymers that form hydrogels such as Carbopol.® acidic carboxy polymers having a molecular weight of 450,000 to 4,000,000; Cyanamer.® polyacrylamides; cross-linked water swellable indene-maleic anhydride polymers; Good-rite.® polyacrylic acid having a molecular weight of 80,000 to 200,000; Polyox.® polyethylene oxide polymers having a molecular weight of 100,000 to 5,000,000; starch graft copolymers; Aqua-Keeps.® acrylate polymer; diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in Handbook of Common Polymers, by Scott and Roff, published by the Chemical Rubber Company, Cleveland, Ohio. The amount of osmopolymer in the first osmotic composition is about 0.01 to 90%, and the amount of osmopolymer in the second osmotic composition is 15 to 95%. In a presently preferred embodiment, the osmopolymer identified as $P_1$ comprising the first composition can be different than the osmopolymer identified as $P_2$ comprising the second composition. The osmopolymer in the first composition can be structurally different than the osmopolymer in the second composition, or the osmopolymers can be substantially structurally identical with the molecular weight of the osmopolymer in the second osmotic composition larger than the molecular weight of the osmopolymer in the first osmotic composition. The osmopolymer $P_1$ comprising the first composition serves as a pharmaceutically acceptable carrier for the active agent and it contributes to the driving force that cooperates with osmopolymer $P_2$ comprising the second composition that delivers the agent through the passageway from the device. During operation of the device fluid is imbibed into the device resulting in the viscosity of $P_2$ being greater than the viscosity of $P_1$. In this operation $P_1$ and $P_2$ operate as a single unit substantially free of a void between the interfaced contacting surfaces of osmopolymer $P_1$ and $P_2$ for successful delivery of the beneficial agent from the osmotic device.

The materials used in forming the semipermeable membrane can be substantially insoluble in the external fluid or they can erode after a predetermined period of time with erosion taking place at the end of the gabapentin release period. Suitable materials include, by way of illustration and not limitation: acetaldehyde dimethyl acetate and acetaldehyde dimethylcellulose acetate; agar acetate; alkylene oxide and alkyl glycidyl ether copolymers; amylose triacetate; beta glucan acetate and beta glucan triacetate; cellulosic materials, which include cellulose esters (e.g., mono-, di- and tricellulose acetates, cellulose acetate butyl sulfonate, cellulose acetate butyrate, cellulose acetate chloroacetate, cellulose acetate dimethylaminoacetate, cellulose acetate ethyl carbamate, cellulose acetate ethyl carbonate, cellulose acetate ethyl oxalate, cellulose acetate laurate, cellulose acetate methyl carbamate, cellulose acetate methyl sulfonate, cellulose acetate octate, cellulose acetate phthalate, cellulose acetate propionate, cellulose acetate succinate, cellulose acetate p-toluene sulfonate, cellulose acetate valerate, cellulose propionate, cellulose propionate succinate, dimethyl cellulose acetate, mono-, di- and tricellulose acrylates, mono-, di- and tricellulose alkanylates, mono, di and tricellulose aroylates, cellulose triacylates such as cellulose trilaurate, cellulose tripalmitate, cellulose trisuccinate and cellulose trivalerate, and cellulose diacylates such as cellulose dicaprylate, cellulose dioctanoate, cellulose dipalmatate, cellulose dipentanlate and cellulose disuccinate), cellulose ethers (e.g., ethyl cellulose, hydroxyethylcellulose, hydroxypropylcellulose, and methylcellulose), cellulose ester-ether polymers, mono-, di- and tricellulose acrylates, mono-, di- and tricellulose alkenylates; hydroxylated ethylene-vinyl acetate; permselective aromatic nitrogen containing polymeric membranes that exhibit water permeability and essentially no solute permeability; polyamides; polyalkylene oxides such as crosslinked and non-crosslinked polyethylene oxide; polyether and polyamide copolymers; polyglycolic acid and polylactic acid and derivatives thereof; polymeric epoxides; poly (methacrylate) copolymer salts such as poly(ammonium methacrylate) copolymer, poly(aminoalkyl methacrylate) copolymer, and (ethyl acrylate)-(methyl methacrylate)-[(trimethylammonium)-ethylmethacrylate] (1:2:0.2) copolymer; cross-linked poly(sodium styrene sulfonate); crosslinked polystyrenes; polyurethanes; polyvinyl alcohol; crosslinked poly(vinylbenzyltrimethyl ammonium chloride); polyvinyl chloride; poly(vinylmethyl ether) copolymers; polyvinylpyrrolidone; propylcarbamate; sulfonated polystyrenes; triacetate of locust gum bean; and so forth; and combinations thereof.

Preferred materials for use in forming the semipermeable membrane, include, by way of illustration and not limitation: cellulose esters, cellulose ethers, polyvinylpyrrolidone, polyvinyl alcohol, polyalkylene oxides, and combinations thereof.

The semipermeable membrane may also include one or more plasticizers, including: acetylated monoglycerides; dibutyl phthalate, diethyl phthalate, isopropyl phthalate, dimethyl phthalate, and dactyl phthalate; dibutyl sebacate and dimethyl sebacate; esters such as acetyl triethyl citrate, acetyl tributyl citrate, citrate ester, dibutyl sebacate, tetraethyl acetate, triethyl citrate and other citrate esters; fatty acids such as stearic acid; glyceryl behenate; glycols such as 1,2-butylene glycol, 2,3-butylene glycol, diethylene glycol, ethylene glycol, propylene glycol, tetraethylene glycol, triethylene glycol and polyalkyleneglycols such as polyethyleneglycol; oils such as castor oil and fractionated coconut oil; glycerin; glycerol and glycerol monostearate; triacetin; and so forth; and combinations thereof.

Preferred plasticizers include esters and fatty acids.

A particularly well-suited example of a core/coating system that can be used with gabapentin to provide for a gastric retained dosage form is the delayed release tablet described in U.S. Pat. No. 6,350,471 to Seth, which comprises a drug/excipient core and a coating of a water-insoluble, water-permeable film-forming polymer such as ethyl cellulose, a plasticizer such as stearic acid, and a water-soluble polymer such as polyvinylpyrrolidone or hydroxypropylcellulose.

Another suitable core/coating system has a polyvinyl alcohol coating, which is either a water soluble polyvinyl alcohol blended with a water insoluble polyvinyl alcohol, or a polyvinyl alcohol that has been crosslinked with a material such as boric acid or sodium borate. Such a coating may also include one or more plasticizers.

For those embodiments of the invention that include further administering additional therapeutic agents simultaneously with gabapentin, these agents can either be administered in the gastric retained dosage form that includes gabapentin or can be administered in a dosage form that is separate from gabapentin. Exemplary dosage forms are described below.

G. Dosage Form of Additional Agents

For those embodiments of the invention that include further administering one or more additional therapeutic agents, such dosages can be any suitable formulation as are well known in the art. For those additional agents where controlled release is desirable, the agent may be incorporated in the gabapentin gastric retained dosage form or be administered in a separate gastric retained or other controlled release formulation dosage form. For those additional agents where immediate release is desirable, the agent may be incorporated in a coating around the gabapentin gastric retained dosage form or in a separate layer of a bilayer tablet, the agent may be simply enclosed in the capsule of the aforementioned gabapentin gastric retained capsule dosage form, or the agent may be administered in a separate immediate release dosage form.

Typically, dosage forms contain the additional agent (another anti-epileptic or anticonvulsant agent) in combination with one or more pharmaceutically acceptable ingredients. The carrier may be in the form of a solid, semi-solid or liquid diluent, or a capsule. Usually the amount of active agent is about 0.1-95 wt %, more typically about 1-50 wt %. Actual methods of preparing such dosage forms are known, or will be apparent, to those skilled in this art; for example, see Remington's Pharmaceutical Sciences, Mack Publishing Company, Easton, Pa., 18th Edition, 1990. The dosage form to be administered will, in any event, contain a quantity of the additional therapeutic agent(s) in an amount effective to alleviate the symptoms of the subject being treated.

In the preparation of pharmaceutical formulations containing the additional therapeutic agent in the form of dosage units for oral administration the agent may be mixed with solid, powdered ingredients, such as lactose, microcrystalline cellulose, maltodextrin, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets such as chewable and oral disintegrating tablets.

Soft gelatin capsules may be prepared by mixing the active agent and vegetable oil, fat, or other suitable vehicle. Hard gelatin capsules may contain granules of the active agent, alone or in combination with solid powdered ingredients such as lactose, saccharose, sorbitol, mannitol, potato starch, corn starch, amylopectin, cellulose derivatives or gelatin.

Liquid preparations for oral administration may be prepared in the form of syrups or suspensions, e.g. solutions or suspensions containing about 0.2-20 wt % of the active agent and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

When the method of the invention includes administering another anti-epileptic or an anticonvulsant agent, there are numerous commercially available dosage forms that can be administered. In addition, other formulations can be readily designed based upon knowledge in the art, and include the gastric-retained delivery systems described above.

Typical dosage forms of the other anti-epileptics or anticonvulsants suitable for use in the invention include tablets, capsules, oral suspensions and syrup. One of skill in the art can readily prepare one of these exemplary formulations or the other anti-epileptic can be administered by means of one of the numerous commercially available products, examples of which are provided below.

Commercially available hydantoin anticonvulsants include, for example, Peganone® (ethotoin, Abbott); Mesantoin® (mephenyloin, Sandoz); and Dilantin® (phenyloin, Warner-Lambert).

Typical dosage forms of the antineuralgics suitable for use in the invention include tablets, capsules and oral suspensions. One of skill in the art can readily prepare one of these exemplary formulations or the antineuralgic can be administered by means of one of the numerous commercially available products, examples of which are provided below.

Commercially available antineuralgics include, for example, Atretol® (carbamazepine, Elan).

Although specific examples of suitable anti-epileptic, anticonvulsant agent and antineuralgic formulations are described above, it is understood that the invention is not limited to those examples as there are numerous other formulations that can be used to deliver the other anti-epileptic or anticonvulsant agents.

The general methods of the invention are best understood with reference to the following examples which are intended to enable those skilled in the art to more clearly understand and to practice the present invention. These examples are not intended, nor are they to be construed, as limiting the scope of the invention, but are merely illustrative and representative thereof.

EXAMPLES

Example 1

Tablets were manufactured using a dry blend process, and hand made on a Carver 'Auto C' Press (Fred Carver, Inc., Indiana). The dry blend process consisted of blending all of the ingredients in a plastic bag, and compressing into a 1000 mg tablet (600 mg gabapentin dose) using a 0.7086"×0.3937" Mod Oval die (Natoli Engineering). The parameters for the operation of the Carver 'Auto C' Press were as follows: 4000 lbs. force, 0 second dwell time (the setting on the Carver Press), and 100% pump speed.

| | Formulation Composition (wt %) | | | |
|---|---|---|---|---|
| Sample # | Active | PEO Coagulant | Methocel K100M | M. St. |
| 1 | 60.0 | 39.0 | 0.0 | 1 |
| 2 | 60.0 | 24.3 | 14.7 | 1 |
| 3 | 60.0 | 0.0 | 39.0 | 1 | where:
Active = gabapentin
PEO Coagulant = poly(ethylene oxide), grade PolyOx Coagulant, NF FP grade, manufactured by Union Carbide/Dow Chemical Company
Methocel K100M = hydroxypropylmethylcellulose, grade Methocel K100M, premium, manufactured by Dow Chemical Company
M. St. = magnesium stearate, NF, supplied by Spectrum Chemical Company The dissolution was determined in USP apparatus 1 (40 mesh baskets), 100 rpm, in deionized water. Samples, 5 ml at each time-point, were taken without media replacement at 1, 4 and 8 hours.

The resulting cumulative dissolution profile, based upon a theoretical percent active added to the formulations is presented in tabulated form below:

| Time | Theoretical (wt %) of Active Released | | |
|---|---|---|---|
| (hours) | Sample 1 | Sample 2 | Sample 3 |
| 1 | 15.4 | 14.8 | 18.6 |
| 4 | 39.4 | 37.4 | 43.3 |
| 8 | 61.7 | 57.8 | 64.7 |

Example 2

Tablets were manufactured using a dry blend process, and hand made on a Carver 'Auto C' Press (Fred Carver, Inc., Indiana). The dry blend process consisted of blending all of the ingredients in a plastic bag, and compressing into a 600 mg tablet (300 mg gabapentin) using a 0.6299"×0.3937" Mod Oval die (Natoli Engineering). The parameters for the operation of the Carver 'Auto C' Press were as follows: ~2000-2500 lbs. force, 0 second dwell time (the setting on the Carver Press), and 100% pump speed.

| | Formulation Composition (wt %) | | | |
|---|---|---|---|---|
| Sample # | Active | PEO Coagulant | Methocel K15M | M. St. |
| 4 | 50.0 | 24.5 | 24.50 | 1 | where:
Active = gabapentin
PEO Coagulant = poly(ethylene oxide), grade PolyOx Coagulant, NF FP grade, manufactured by Union Carbide/Dow Chemical Company
Methocel K15M = hydroxypropylmethylcellulose, grade Methocel K15M, premium, manufactured by Dow Chemical Company
M St. = magnesium stearate, NF, supplied by Spectrum Chemical Company The dissolution was determined in USP apparatus 1 (40 mesh baskets), 100 rpm, in deionized water. Samples, 5 ml at each time-point, were taken without media replacement at 1, 2, 4 and 8 hours.

The resulting cumulative dissolution profile, based upon a theoretical percent active added to the formulation is presented in tabulated form below:

| Time (hours) | Theoretical wt % of Active Released Sample 4 |
|---|---|
| 1 | 20.6 |
| 2 | 32.4 |
| 4 | 49.7 |
| 6 | 63.1 |
| 8 | 74.0 |
| 10 | 82.6 |

Example 3

Three Gastric Retentive (GR™) gabapentin formulas were manufactured utilizing a standard granulation technique. The formulations manufactured are shown in tabulated form below.

| Formulation for Clinical Trial Manufacture | | |
|---|---|---|
| Gabapentin GR8, 300-mg (GR8, 300-mg) | Gabapentin GR6, 300-mg (GR6, 300-mg) | Gabapentin GR8, 600-mg (GR8, 600-mg) |
| 44.76% Gabapentin | 44.76% Gabapentin | 61.11% Gabapentin |
| 21.99% Methocel ® K15M, premium | 16.46% Methocel ® K4M, premium | 7.59% Methocel ® K15M, premium |
| 21.99% Sentry ® PolyOx ® WSR Coagulant, NF FP | 21.99% Sentry ® PolyOx ® WSR 303, NF FP | 27.09% Sentry ® PolyOx ® WSR 303, NF FP |
| 7.49% Avicel ® PH-101, NF | 12.98% Avicel ® PH-101, NF | 0.00% Avicel ® PH-101, NF |
| 2.75% Methocel ® E5, prem. | 2.75% Methocel ® E5, prem. | 3.22% Methocel ® E5, prem. |
| 1.00% Magnesium Stearate, NF | 1.00% Magnesium Stearate, NF | 1.00% Magnesium Stearate, NF |
| 670-mg | 670-mg | 982-mg |
| 0.3937" × 0.6299" Mod Oval | 0.3937" × 0.6299" Mod Oval | 0.4062" × 0.75" Mod Cap |

Gabapentin was obtained from Plantex U.S.A. (Englewood Cliffs, N.J.). Methocel® brand hydroxypropyl methylcellulose (also known as hypromellose), and Sentry® PolyOx® brand polyethylene oxide were obtained from Dow Chemical (Midland, Mich.). Methocel E5, premium is a USP type 2910 hydroxypropyl methylcellulose with number average molecular weight of on the order of 6000-8000 and a viscosity of 5 cps as a 2% aqueous solution at 20° C. Methocel® K4M and Methocel® K15M are USP type 2208 hydroxypropyl methylcellulose with viscosities of 4000 cps and 15,000 cps, respectively, as a 2% aqueous solution at 20° C., and number average molecular weights on the order of 80,000 and 100,000, respectively. Sentry PolyOx® WSR 301, NF FP, Sentry® PolyOx® WSR Coagulant, NF FP and Sentry® PolyOx® WSR 303, NF FP have viscosity-average molecular weights of approximately 4,000,000, 5,000,000 and 7,000,000, respectively. Avicel PH-101, NF is microcrystalline cellulose supplied by FMC Corporation (Philadelphia, Pa.). Magnesium stearate, NF was supplied by Spectrum Quality Products (New Brunswick, N.J.).

The dissolution profiles, as determined by USP Apparatus 1 (100 rpm) in modified simulated gastric fluid, for three prototypes GR™ formulations are shown in FIG. 1.

Example 4

Figure 2:
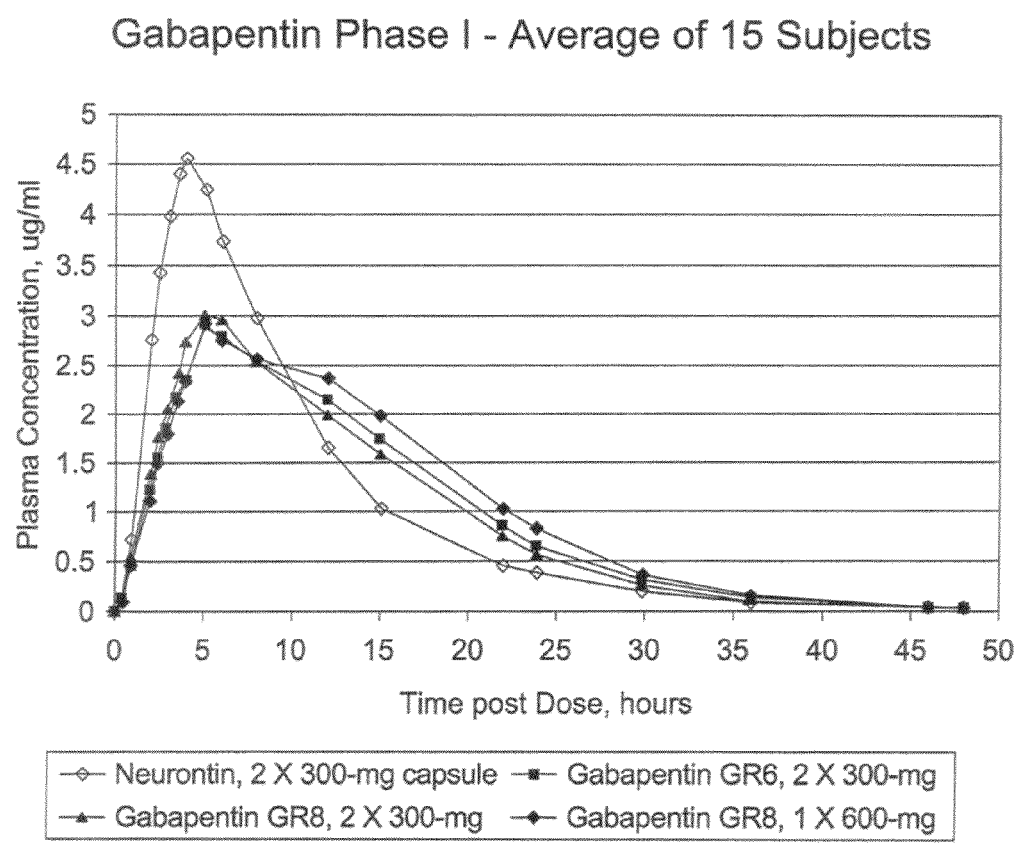
FIG. 2 illustrates the average plasma profile of three GR™ formulations and Neurontin®.

The pharmacokinetic profiles of the three formulations described in Example 3, administered as a 600-mg dose, were compared to Neurontin® immediate release 300-mg capsule in a randomized four-way cross-over experiment involving 15 healthy volunteers. Each subject was administered treatment of 600-mg gabapentin as one of the three GR™ formulations (1×600-mg tablet or 2×300-mg tablet) or Neurontin® capsules (2×300-mg) within 5 minutes of completing a high fat breakfast (FDA breakfast). Plasma samples were taken up to 48 hours post-dose. FIG. 2 illustrates the average plasma profile for the four treatments administered, and the pharmacokinetic data are summarized in tabulated form below.

| Gabapentin Plasma Data—Average for 15 Subjects | | | | |
|---|---|---|---|---|
| Dosing | | $AUC_{inf}^{\#}$ (µg/ml)*hr) | $C_{max}^{\#}$ (µg/ml) | $T_{max}$ (hours) |
| Nerontin ®, 300-mg | Mean | 46.65 | 4.72 | 3.93 |
| 2 x capsules | % CV | 19.0 | 20.2 | 15.1 |
| GR6, 300-mg | Mean | 44.43 | 2.97 | 6.63 |
| 2 x tablets | % CV | 34.9 | 29.7 | 45.1 |
| GR8, 300-mg | Mean | 41.84 | 3.10 | 5.63 |
| 2 x tablets | % CV | 34.4 | 26.2 | 34.9 |
| GR8, 600-mg | Mean | 48.01 | 3.13 | 7.13 |
| 1 x tablet | % CV | 26.8 | 18.7 | 42.2 |

$^{\#}$Geometric Mean and Geometric % CV are reported here

As demonstrated in FIG. 2 and in tabulated form above, GR™ formulations demonstrate sustained release with a lower maximum plasma concentration and a larger value for the time of the maximum concentration compared to the immediate release capsules without loss in the bioavailability as measured by the plasma $AUC_{inf}$.

Example 5

A tablet containing 900 mg of gabapentin is prepared by granulation with 90 mg of polyvinylpyrrolidone and 10 mg of magnesium stearate and then tableted as a 1000 mg tablet on a Carver press with 4000 lbs force, 0 second dwell time. These tablet cores are then coated from an alcohol-water solution that dries with approximately 2% dry coat weight of 10 mg ethyl cellulose, 7 mg Povidone (PVP), and 3 mg stearic acid.

Example 6

A tablet containing 1200 mg of gabapentin is prepared by granulation with 120 mg of polyvinylpyrrolidone and 10 mg of magnesium stearate and then tableted as a 1330 mg tablet on a Carver press with 4000 lbs force, 0 second dwell time. These tablet cores are then coated from an alcohol-water solution that dries with approximately 25 mg dry coat weight of 10 mg ethyl cellulose, 10 mg hydroxypropylcellulose, and 5 mg glyceryl behenate.

Example 7

A tablet containing 900 mg of gabapentin is prepared by granulation with 90 mg of polyvinylpyrrolidone and 10 mg of magnesium stearate and then tableted as a 1000 mg tablet on a Carver press with 4000 lbs force, 0 second dwell time. These tablet cores are then coated from an aqueous solution that dries with approximately 2% dry coat weight of 15 mg polyvinyl alcohol (PVA), 5 mg Povidone (PVP), and 3 mg stearic acid. The coated tablets are then sprayed with an aqueous solution of 1% sodium borate to crosslink the PVA and dried.

Example 8

A tablet containing 900 mg of gabapentin is prepared by granulation with 90 mg of polyvinylpyrrolidone, 250 mg microcrystalline cellulose, and 10 mg of magnesium stearate and then tableted as a 1250 mg tablet on a Carver press with 4000 lbs force, 0 second dwell time. These tablet cores are then coated from an alcohol-water solution that dries with approximately 2% dry coat weight of 10 mg ethyl cellulose, 7 mg Povidone (PVP), and 3 mg stearic acid.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. An oral dosage form, comprising
   an osmotic device comprising a core comprising gabapentin, and a semipermeable membrane surrounding the core, wherein the semipermeable membrane comprises a plasticizer, is permeable to a fluid in an environment of use and is substantially impermeable to unsolubilized gabapentin,
   wherein the oral dosage form as formulated is of sufficient size to promote retention in the stomach of a subject in the fed mode for a period of at least about 5 hours,
   wherein the dosage form is a tablet comprising about 100 mg to about 4800 mg gabapentin,
   wherein the gabapentin is released into the upper gastrointestinal tract over a period of about 5-12 hours at a rate sufficient to achieve a lower maximum plasma concentration ($C_{max}$) compared to an equal dose of gabapentin provided by an immediate release dosage form.

2. The dosage form of claim 1, wherein the dosage form provides bioavailability of gabapentin at a level greater than or equal to 80 % of that provided by an equal dose of gabapentin released by the immediate release dosage form as measured by the plasma $AUC_{inf}$.

3. The dosage form of claim 1, wherein the osmotic device comprises an elementary pump.

4. The dosage form of claim 1, wherein the dosage form comprises about 300 mg or about 600 mg gabapentin.

5. The dosage form of claim 1, further comprising a second therapeutic agent selected from the group consisting of a hydantoin, an iminostilbene, a valproate, a phenyltriazine, a barbiturate, a deoxybarbiturate, a benzodiazepine, a carbamate, an anticonvulsant other than gabapentin, a tricyclic antidepressant, levadopa, carbidopa, an opioid, lithium, carbamazepine, valproate, trifluoperazine, clonazepam, risperidone, lorazepam, venlafaxine, clozapine, olanzapine, a benzodiazepine, a neuroleptic, a serotonin reuptake inhibitor, buproprion, nefadone, venlaxatine, nefadone, diazepam, oxazepam, a dopaminergic agent, clonazepam, a triptan and ergotamine.

6. The dosage form of claim 1, wherein the osmotic device comprises a push-pull osmotic device comprising a first osmotic composition and a second osmotic composition housed in a compartment of the push-pull osmotic device.

7. The dosage form of claim 6, wherein the dosage form provides for bioavailability of gabapentin at a level greater than or equal to 80 % of that provided by an equal dose of gabapentin released by the immediate release dosage form as measured by the plasma $AUC_{inf}$.

8. The dosage form of claim 6, wherein the dosage form comprises about 300 mg or about 600 mg gabapentin.

9. The dosage form of claim 6, further comprising a second therapeutic agent selected from the group consisting of a hydantoin, an iminostilbene, a valproate, a phenyltriazine, a barbiturate, a deoxybarbiturate, a benzodiazepine, a carbamate, an anticonvulsant other than gabapentin, a tricyclic antidepressant, levadopa, carbidopa, an opioid, lithium, carbamazepine, valproate, trifluoperazine, clonazepam, risperidone, lorazepam, venlafaxine, clozapine, olanzapine, a benzodiazepine, a neuroleptic, a serotonin reuptake inhibitor, buproprion, nefadone, venlaxatine, nefadone, diazepam, oxazepam, a dopaminergic agent, clonazepam, a triptan and ergotamine.

10. The dosage form of claim 1, wherein the osmotic device comprises a macroporous membrane.

11. The dosage form of claim 10, wherein the dosage form provides for bioavailability of gabapentin at a level greater than or equal to 80 % of that provided by an equal dose of gabapentin released by the immediate release dosage form as measured by the plasma $AUC_{inf}$.

12. The dosage form of claim 10, wherein the dosage form comprises about 300 mg or about 600 mg gabapentin.

13. The dosage form of claim 10, further comprising a second therapeutic agent selected from the group consisting of a hydantoin, an iminostilbene, a valproate, a phenyltriazine, a barbiturate, a deoxybarbiturate, a benzodiazepine, a carbamate, an anticonvulsant other than gabapentin, a tricyclic antidepressant, levadopa, carbidopa, an opioid, lithium, carbamazepine, valproate, trifluoperazine, clonazepam, risperidone, lorazepam, venlafaxine, clozapine, olanzapine, a benzodiazepine, a neuroleptic, a serotonin reuptake inhibitor, buproprion, nefadone, venlaxatine, nefadone, diazepam, oxazepam, a dopaminergic agent, clonazepam, a triptan and ergotamine.

14. The dosage form of claim 1, wherein the plasticizer is selected from acetylated monoglycerides, dibutyl phthalate, diethyl phthalate, isopropyl phthalate, dimethyl phthalate, dactyl phthalate, dibutyl sebacate, dimethyl sebacate, esters, fatty acids, glycols, oils, glycerin, glycerol, glycerol monostearate, and triacetin.

15. The dosage form of claim 14, wherein the plasticizer is selected from esters and fatty acids.

16. The dosage form of claim 15, wherein the ester is selected from the group consisting of acetyl triethyl citrate, acetyl tributyl citrate, citrate ester, dibutyl sebacate, tetraethyl acetate, and triethyl citrate.

17. The dosage form of claim 15, wherein the fatty acid is a stearic acid.

18. The dosage form of claim 1, wherein the subject is a human.

* * * * *